(12) United States Patent
Darcy et al.

(10) Patent No.: US 9,005,635 B2
(45) Date of Patent: Apr. 14, 2015

(54) ARTICLES AND PROCESSES FOR MAKING A POROUS DISINTEGRATABLE SOLID SUBSTRATE FOR PERSONAL HEALTH CARE APPLICATIONS

(75) Inventors: Trevor John Darcy, West Chester, OH (US); Steven Ray Gilbert, Fairfield, OH (US); Robert Wayne Glenn, Jr., Liberty Township, OH (US); Mark Edward Stella, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 209 days.

(21) Appl. No.: 13/409,137

(22) Filed: Mar. 1, 2012

(65) Prior Publication Data

US 2012/0225100 A1 Sep. 6, 2012

Related U.S. Application Data

(60) Provisional application No. 61/447,737, filed on Mar. 1, 2011, provisional application No. 61/447,738, filed on Mar. 1, 2011.

(51) Int. Cl.
| | | |
|---|---|---|
| *A61K 9/00* | (2006.01) | |
| *A61K 9/20* | (2006.01) | |
| *A61K 9/70* | (2006.01) | |
| *A61K 47/32* | (2006.01) | |
| *A23L 1/30* | (2006.01) | |

(52) U.S. Cl.
CPC ............. *A61K 9/0095* (2013.01); *A61K 9/0056* (2013.01); *A61K 9/006* (2013.01); *A61K 9/2027* (2013.01); *A61K 9/7007* (2013.01); *A61K 47/32* (2013.01); *A23L 1/30* (2013.01)

(58) Field of Classification Search
None
See application file for complete search history.

(56) References Cited

U.S. PATENT DOCUMENTS

| | | | |
|---|---|---|---|
| 4,642,903 A | 2/1987 | Davies et al. | |
| 5,776,491 A * | 7/1998 | Allen et al. | 424/465 |
| 6,090,401 A | 7/2000 | Gowan et al. | |
| 6,150,424 A | 11/2000 | Breitenbach et al. | |
| 6,451,348 B1 * | 9/2002 | Jeong et al. | 424/486 |
| 6,800,668 B1 | 10/2004 | Odidi et al. | |
| 6,964,771 B1 | 11/2005 | Roser et al. | |
| 7,074,431 B2 | 7/2006 | Busson et al. | |
| 7,621,300 B2 | 11/2009 | Bonney et al. | |
| 8,268,764 B2 * | 9/2012 | Glenn et al. | 510/120 |
| 2003/0040487 A1 | 2/2003 | Santar et al. | |
| 2003/0072804 A1 | 4/2003 | Hird et al. | |
| 2004/0028732 A1 | 2/2004 | Von Falkenhausen et al. | |
| 2004/0071755 A1 | 4/2004 | Fox et al. | |
| 2005/0202090 A1 | 9/2005 | Clarke | |
| 2007/0225388 A1 | 9/2007 | Cooper et al. | |
| 2009/0010983 A1 | 1/2009 | Melvik et al. | |
| 2009/0087486 A1 | 4/2009 | Krumme et al. | |
| 2009/0148501 A1 | 6/2009 | Hofacker et al. | |
| 2009/0232873 A1 * | 9/2009 | Glenn et al. | 424/443 |
| 2009/0263342 A1 | 10/2009 | Glenn, Jr. et al. | |
| 2010/0080829 A1 * | 4/2010 | Dulieu et al. | 424/400 |
| 2010/0167971 A1 * | 7/2010 | Glenn et al. | 510/101 |
| 2010/0173817 A1 | 7/2010 | Glenn, Jr. et al. | |
| 2010/0179083 A1 | 7/2010 | Glenn, Jr. et al. | |
| 2010/0279905 A1 | 11/2010 | Glenn, Jr. et al. | |
| 2010/0286011 A1 | 11/2010 | Glenn, Jr. et al. | |
| 2010/0291165 A1 | 11/2010 | Glenn, Jr. et al. | |
| 2010/0298188 A1 | 11/2010 | Glenn, Jr. et al. | |
| 2011/0023240 A1 | 2/2011 | Glenn, Jr. et al. | |
| 2011/0027328 A1 * | 2/2011 | Baig et al. | 424/401 |
| 2011/0028373 A1 | 2/2011 | Fossum et al. | |
| 2011/0028374 A1 | 2/2011 | Glenn, Jr. et al. | |
| 2011/0132387 A1 | 6/2011 | Alwattari et al. | |
| 2011/0182956 A1 | 7/2011 | Glenn, Jr. et al. | |
| 2011/0189246 A1 | 8/2011 | Glenn, Jr. et al. | |
| 2011/0189247 A1 | 8/2011 | Glenn, Jr. et al. | |
| 2011/0195098 A1 | 8/2011 | Glenn, Jr. et al. | |
| 2011/0200649 A1 | 8/2011 | Schwartz | |
| 2012/0021026 A1 | 1/2012 | Glenn, Jr. et al. | |
| 2012/0052036 A1 | 3/2012 | Glenn, Jr. et al. | |
| 2012/0237576 A1 | 9/2012 | Gordon et al. | |

OTHER PUBLICATIONS

PCT International Search Report mailed Jun. 6, 2012—5 pages.

* cited by examiner

*Primary Examiner* — Carlos Azpuru
*Assistant Examiner* — Casey Hagopian
(74) *Attorney, Agent, or Firm* — Alexandra S. Anoff

(57) ABSTRACT

A personal health care article. More particularly, a personal health care article comprising at least one porous disintegratable solid substrate comprising: from about 1% to about 70%, by weight of said substrate, of a surfactant, from about 10% to about 70%, by weight of said substrate, of one or more polymers, from about 0.025% to about 85%, by weight of said substrate, of one or more health care actives, optionally a plasticizer, and optionally an aesthetic agent wherein said article is ingestible. The invention also comprises a process for making a personal health care article.

22 Claims, No Drawings

ARTICLES AND PROCESSES FOR MAKING A POROUS DISINTEGRATABLE SOLID SUBSTRATE FOR PERSONAL HEALTH CARE APPLICATIONS

CROSS REFERENCE TO RELATED APPLICATIONS

This application claims the benefit of U.S. Provisional Application No. 61/447,737, filed Mar. 1, 2011 and U.S. Provisional Application No. 61/447,738, filed Mar. 1, 2011.

FIELD OF THE INVENTION

The present invention relates to personal health care articles, especially those personal health care articles providing health benefits that can comprise at least one porous disintegratable solid substrate, a surfactant, and a polymer. The invention further relates to articles and processes of making an article as described herein.

BACKGROUND OF THE INVENTION

Many personal health care products in the market today are sold containing water. The water in the formula adds to the weight and size of the products and translates into greater shipping and storage costs. Additionally, these types of products also have disadvantages in terms of packaging, storage, transportation, and convenience of use. It can also be difficult to control the dosing of liquid personal health care products. Moreover, the presence of water in personal health care products increases susceptibility to degradation of water unstable ingredients and promotes negative interactions between two or more incompatible materials in an article.

Some personal health care products are swallowable and sold as capsules, pills, caplets, and tablets and consumers need a drink, such as water, to ingest the product. It can be inconvenient for a consumer to find a drink to consume a personal health care product in this form. Other personal health care products are chewable and sold as tablets. These chewable tablets do not require a drink for ingestion. However, they are not durable and tend to break when the consumer transports them and often have a chalky flavor.

Some personal health care products are available in a dissolvable strip. However, these strips have a low loading capacity which limits the variety and amount of personal health care actives that can be added to the dosage form.

Therefore, a need exists for personal health care articles that do not contain a liquid, can be ingested by the consumer without a drink, are durable during transport, and can contain broad ranges of health care actives and aesthetic agents, which includes higher levels of health care actives than are currently available in dissolvable strips. The porous disintegratable solid substrates and articles of this invention interact with the moisture in the oral cavity to disintegrate and release the health care active(s) and/or aesthetic agent(s) which are then ingested by the consumer.

SUMMARY OF THE INVENTION

An embodiment is directed to a personal health care article comprising at least one porous disintegratable solid substrate comprising: (a) from about 1% to about 70%, by weight of said substrate, of a surfactant; (b) from about 10% to about 70%, by weight of said substrate, of one or more polymers; (c) from about 0.025% to about 85%, by weight of said substrate, of one or more health care actives; and (d) optionally a plasticizer; wherein said article is ingestible.

An additional embodiment relates to a personal health care article comprising at least one porous disintegratable solid substrate comprising: (a) from about 1% to about 70%, by weight of said substrate, of a surfactant; (b) from about 10% to about 70%, by weight of said substrate, of one or more polymers; (c) from about 0.001% to about 80%, by weight of said substrate, of one or more aesthetic agents; and optionally a plasticizer; wherein said article is ingestible.

An additional embodiment relates to a process of making a personal health care article comprising the steps of: (a) preparing a mixture comprising from about 1% to about 70% of a surfactant, from about 10% to about 70% of one or more polymers, and from about 0.025% to about 85% of one or more health care actives; (b) introducing a gas into said mixture to form a wet aerated mixture; (c) shaping said wet aerated mixture into at least one shaped wet mixture; (d) drying at least one shaped wet mixture; and (e) forming a porous disintegratable solid substrate having a final moisture content of from about 0.5% to about 15% moisture.

An additional embodiment relates to a process of making a personal health care article comprising the steps of: (a) preparing a mixture comprising from about 1% to about 70% of a surfactant and from about 10% to about 70% of one or more polymers; (b) introducing a gas into said mixture to form a wet aerated mixture; (c) shaping said wet aerated mixture into at least one shaped wet mixture; (d) drying at least one shaped wet mixture; and (e) forming a porous disintegratable solid substrate having a final moisture content of from about 0.5% to about 15% moisture; and (f) applying a surface resident coating comprising one or more health care actives to said porous disintegratable solid substrate.

DETAILED DESCRIPTION OF THE INVENTION

An embodiment of the invention can be directed towards a personal health care article that may comprise at least one porous disintegratable solid substrate comprising: (a) a surfactant; (b) a polymer; (c) one or more health care actives; and (d) optionally a plasticizer; wherein said article is ingestible.

These and other limitations of the articles, process, and methods of the present invention, as well as many of the optional ingredients suitable for use herein, are described in detail hereinafter.

As used herein, the term "disintegratable" and "disintegration" means that the personal health care article or substrate is reduced to components, fragments or particles. In one example, the personal health care article can be dissolvable. As used herein, "disintegratable" means that the porous dissolvable solid substrate has a disintegration rate that satisfies the Disintegration Rate Method described herein.

As used herein, the term "dissolution" refers to the health care active dissolving into solution. The "dissolution rate" is the amount of time it takes for the health care article to disintegrate and for the active to dissolve and go into solution. The dissolution rate can be measured by the Dissolution Rate Method described herein.

As used herein, the term "ingestible" as used herein refers to personal health care articles in a form that is deliverable to a mammal in need via the oral cavity, mouth, throat, nasal passage, rectum, vagina, skin and combinations thereof.

As used herein "delayed release health care actives" refers to health care actives that are released at a time later than that immediately following its administration.

As used herein "extended release health care actives" refers to a health care active wherein the health care active is slowly released over time.

As used herein "immediate release health care actives" refers to health care actives wherein the health care active is released immediately or soon after its administration.

As used herein, the term "open cell", refers to a solid, interconnected, polymer-containing matrix that defines a network of spaces or cells that contain a gas, such as air.

As used herein, the term "closed cell", refers to a solid, polymer containing matrix that defines a network of spaces or cells that contain a gas, such as air, where the spaces or cell are not interconnected.

As used herein, the term "applying" includes spraying, dusting, sprinkling, coating, surface-printing (e.g., in the shape of a desired adornment, decoration, or pattern), pouring on, injecting into the interior, dipping, or by any other suitable means, such as by use of a depositor, sifter, or powder bed.

As used herein, the term "orally administering" and/or "administering" with respect to the human/mammal means that the human/mammal ingests or is directed to ingest (whether by swallowing, spraying or any other means) one or more of the personal health care articles. The human/mammal may be directed to deliver the personal health care article to the site that the human/mammal intends to treat, for example, the oral mucosa. The human/mammal may be directed to ingest the personal health care article, and such direction and or delivery may be that which instructs and/or informs the human that use of the personal health care article may provide a wellness benefit. The relief can be instant, delayed or extended. For example, such direction may be oral direction (e.g., through oral instruction from, for example, a physician, pharmacist, or other health professional), radio or television media (e.g., advertisement), or written direction (e.g., through written direction from, for example, a physician, pharmacist, or other health professional (e.g., scripts), sales professional organization (e.g., through, for example, marketing brochures, pamphlets, or other instructive paraphernalia), written media (e.g., internet, electronic mail, or other computer-related media)), and/or packaging associated with the personal health care article (e.g., a label present on a delivery device holding the personal health care article). As used herein, "written" means through words, pictures, symbols, and/or other visible or tactile descriptors. Such information need not utilize the actual words used herein, for example, "respiratory", "symptom", or "mammal", but rather use of words, pictures, symbols, tactile means, and the like conveying the same or similar meaning are contemplated within the scope of this invention.

As used herein, the term "treat" or "treating" includes preventing, alleviating, ameliorating, inhibiting, or mitigating one or more health conditions, respiratory symptoms, gastrointestinal symptoms, CNS symptoms, pathogenic infection symptoms, and nutritional deficiency symptoms.

As used herein, the term "prevent", "preventing" or "prevention" includes preventing one or more health care conditions or its associated symptoms from occurring in a mammal, for example when the mammal is predisposed to acquiring the symptoms of coughing, inhibiting the onset of coughing or its associated symptoms; and/or alleviating, reversing, or curing the coughing episode or its associated symptoms.

Health care actives and aesthetic agents useful herein may be categorized or described herein by their health benefit and/or health conditions or their postulated mode of action or function. However, it is to be understood that the health care actives and aesthetic agents useful herein can, in some instances, provide more than one health benefit and/or health conditions or function or operate via more than one mode of action. Therefore, classifications herein are made for the sake of convenience and are not intended to limit an ingredient to the particularly stated function(s) or activities listed.

All weights, measurements and concentrations herein are measured at 25 degrees Celsius (° C.) on the personal health care article, unless otherwise specified.

All percentages, parts and ratios as used herein are by weight of the total personal health care article, unless otherwise specified. All such weights as they pertain to listed ingredients are based on the active level and, therefore do not include solvents or by-products that may be included in commercially available materials, unless otherwise specified.

The article, process and methods of the present invention can comprise, consist of, or consist essentially of, the essential elements and limitations of the invention described herein, as well as any additional or optional ingredients, components, or limitations described herein or otherwise useful in personal health care articles intended for use or consumption by mammals preferably consumption or use by humans.

Personal Health Care Article

The personal health care article can comprise at least one porous disintegratable solid substrate. The personal health care article can be administered directly to a mammal or incorporated into a device. The use of such a personal health care article allows for easy portability and the ability to better control dosing. Once disintegrated, the personal health care article can be ingested by to the consumer. In another embodiment, the personal health care article can be ingested through the nasal passage, rectum, vagina, or skin. In another embodiment, the personal health care article can be a transdermal delivery system which administers health care actives through the skin.

The personal health care article can also be delivered via a water insoluble implement or device. For instance, the personal health care article may be attached or glued by some mechanism to an applicator to facilitate application to the oral cavity, mouth, throat, nasal passage, rectum, vagina, skin i.e., a comb, rag, wand, or any other conceivable water-insoluble applicator. In an embodiment, the personal health care article is placed into a liquid, such as water, disintegrated and then administered to the mammal.

In an embodiment, the personal health care article of the present invention can be a flat article in the form of a pad, strip, tape, or tablet having a thickness of from about 0.5 millimeter (mm) to about 40 mm, in another embodiment from about 1 mm to about 25 mm, in yet another embodiment from about 3 mm to about 15 mm, and in a further embodiment from about 5 mm to about 10 mm, as measured by the Thickness Method described hereafter. In another embodiment, the personal health care article can be rolled into a cylindrical shape. In an embodiment the personal health care article can be cubical and each side has a length from about 5 mm to 30 mm, in another embodiment from about 10 mm to 20 mm, and in a further embodiment from about 12 mm to about 18 mm, as measured by the Thickness Method described hereafter.

The personal health care article has a basis weight of from about 125 grams/meter$^2$ (g/m$^2$) to about 3,000 g/m$^2$, in an embodiment from about 125 g/m$^2$ to about 2,500 g/m$^2$, in another embodiment from about 400 g/m$^2$ to about 2,000 g/m$^2$, in another embodiment from about 500 g/m$^2$ to about 1,500 g/m$^2$ and in another embodiment from about 600 g/m$^2$ to about 1,200 g/m$^2$, and in another embodiment from about 700 g/m$^2$ to about 1,000 g/m$^2$, as measured according to the Basis Weight Method described hereafter.

The personal health care article can be produced in any of a variety of product forms, including porous disintegratable solid substrates used alone or in combination with other consumer product components. Regardless of the form, the key to some embodiments of the product form contemplated within the scope of the method of the present invention is the selected and defined personal health care article may comprises a combination of a polymer and a health care active and/or aesthetic agent, all as defined herein.

The personal health care article may comprise one or more textured, dimpled or otherwise topographically patterned surfaces including letters, logos or figures. The textured personal health care article can result from the shape of the porous disintegratable solid substrate, in that the outermost surface of the article contains portions that are raised with respect to other areas of the surface. The raised portions can result from the formed shape of the personal health care article, for example the porous distintegratable solid substrates of the personal health care article can be formed originally in a dimpled or waffle pattern. The raised portions can also be the result of creping processes, imprinted coatings, embossing patterns, laminating to other substrates having raised portions, or the result of the physical form of the article itself. The texturing can also be the result of laminating one substrate to a second substrate that is textured.

In a particular embodiment, the personal health care article can be perforated with holes or channels penetrating into or through the personal health care article. These perforations can be formed as part of the web making process via spikes extended from the surface of an adjacent belt, drum, roller or other surface. Alternatively, these perforations can be formed after the web making process via poking or sticking the porous solids with pins, needles or other sharp objects.

In an embodiment, the personal health care article is in the form of one or more flat sheets or pads of an adequate size to be able to be handled easily by the user. In another embodiment, the flat sheet or pad contains one dose of one or more health care actives that can provide a health benefit. The personal health care article may have a square, rectangle or disc shape or any other suitable shape. The personal health care article can also be in the form of a continuous strip including delivered on a tape-like roll dispenser with individual portions dispensed via perforations and or a cutting mechanism.

In another embodiment, the porous disintegratable solid substrate(s) are rolled, compressed, cut, or stacked to form a three dimensional personal health care article. For instance, the porous disintegratable solid substrate(s) may be compressed into a pill or tablet, rolled into a cylinder, or compressed or stacked into a cube to form the personal health care article.

In an embodiment, the personal health care article contains more than one porous disintegratable solid substrate. In another embodiment, the personal health care article comprises a first porous disintegratable solid substrate and a second porous disintegratable solid substrate both comprising one or more health care actives and the health care actives can be the same health care active or different health care actives. In another embodiment, the personal health care article comprises a first porous disintegratable solid substrate and a second porous disintegratable solid substrate both comprising one or more aesthetic agents and the aesthetic agents can be the same aesthetic agent or different aesthetic agents. In some embodiments, the personal health care article comprises a first porous disintegratable solid substrate and a second porous disintegratable solid substrate and the first porous disintegratable solid substrate comprises one or more health care actives and the second porous disintegratable solid substrate comprises one or more aesthetic agents. In another embodiment, said personal health care article comprises a first porous disintegratable solid substrate and a second porous disintegratable solid substrate, and the health care active is situated between the first porous disintegratable solid substrate and the second porous disintegratable solid substrate.

The Porous Disintegratable Solid Substrate

The porous disintegratable solid substrate can comprise a surfactant, a polymer, and optionally a plasticizer. In an embodiment, the porous disintegratable solid substrate of the present invention can have a thickness of from about 0.5 mm to about 10 mm, in another embodiment from about 1 mm to about 9 mm, in yet another embodiment from about 2 mm to about 8 mm, and in a further embodiment from about 3 mm to about 7 mm, as measured by the Thickness Method described hereafter.

The porous disintegratable solid substrate can have a basis weight of from about 125 $g/m^2$ to about 1,000 $g/m^2$, in another embodiment from about 150 $g/m^2$ to about 800 $g/m^2$, in an alternate embodiment from about 200 $g/m^2$ to about 700 $g/m^2$, and in still another embodiment from about 300 $g/m^2$ to about 650 $g/m^2$, as determined by the Basis Weight Method described hereafter.

The porous disintegratable solid substrate can have a Cell Wall Thickness of from about from about 0.02 mm to about 0.15 mm, in an embodiment from about 0.025 mm to about 0.12 mm, in another embodiment from about 0.03 mm to about 0.09 mm, and in still another embodiment from about 0.035 mm to about 0.06 mm, as measured according to the Cell Wall Thickness Method described hereafter.

The porous disintegratable solid substrate can have a minimum level of interconnectivity between the cells, which is quantified by the Structure Model Index (SMI) and the Percent Open Cell Content. The porous disintegratable solid substrate can have a SMI of from about 0.0 to about 3.0, in another embodiment from about 0.5 to about 2.75, and in another embodiment from about 1.0 to about 2.50, as measured by the Structure Model Index Method described hereafter. In an embodiment, the porous disintegratable solid substrate can have a Percent Open Cell Content greater than 50%, as measured by the Gas Pycnometry Method described hereafter. In certain embodiments the porous disintegratable solid substrate can have a percent open cell content from about 50% to about 100%, in another embodiment, from about 70% to about 100%, in another embodiment from about 80% to about 100%, in yet another embodiment from about 85% to about 97.5%, and in a further embodiment from about 90% to about 95%, as measured by the Gas Pycnometry Method described hereafter.

The porous disintegratable solid substrate can have a Star Volume of from about 1 $mm^3$ to about 90 $mm^3$, in one embodiment from about 1.5 $mm^3$ to about 60 $mm^3$, in another embodiment from about 2 $mm^3$ to about 30 $mm^3$, and in still another embodiment from about 2.5 $mm^3$ to about 15 $mm^3$.

The porous disintegratable solid substrate can have a dry density of from about 0.03 grams/centimeter$^3$ ($g/cm^3$) to about 0.50 $g/cm^3$, in another embodiment from about 0.05 $g/cm^3$ to about 0.35 $g/cm^3$, in yet another embodiment from about 0.08 $g/cm^3$ to about 0.30 $g/cm^3$, in a further embodiment from about 0.10 $g/cm^3$ to about 0.25 $g/cm^3$, and in another embodiment from about 0.12 $g/cm^3$ to about 0.20 $g/cm^3$, as measured by the Dry Density Method described hereafter.

In another embodiment the porous disintegratable solid substrate can be flexible. In another embodiment, the porous disintegratable solid substrate is rolled, compressed, cut, or stacked into a pill or tablet to form the personal health care article. In another embodiment, the porous disintegratable solid substrate is rolled into a cylindrical shape to form the personal health care article.

The porous disintegratable solid substrate can comprise a surfactant, a polymer, and a health care active. In one example, the ratio of surfactant to polymer is from about 1:10 to about 1:1, in another example from about 1:5 to about 4:5, and in another example from about 3:10 to about 7:10. In one example, the ratio of surfactant to active is from about 1:5 to about 8:1, in another example from about 1:5 to about 6:1, in another example from about 3:10 to about 6:5, and in another example from about 3:10 to about 3:5. In one example, the ratio of health care active to polymer is from about 0.0005 to about 3, in another example from about 1:1000 to about 2:1, in another example from about 1:100 to about 9:5, in another example from about 1:10 to about 8:5, in another example from about 1:10 to about 3:2, and in another example from about 1:2 to about 13:10.

Surfactants

The porous disintegratable solid substrate of the present invention can include a surfactant. In an embodiment, the surfactant can be ingestible. In certain embodiments, the porous disintegratable solid substrates of the present invention can be non-lathering and in other embodiments, the porous disintegratable solid substrates can be lathering. In certain embodiments, the surfactant can aid in processing that helps to generate a wet aerated mixture with the desired properties prior to drying. Non-limiting examples of surfactants that can aid in processing can include polyoxylglycerides, sorbitan esters and other emulsifiers, and combinations thereof. In another embodiment, the porous disintegratable solid substrates can contain a surfactant that also acts as a health care active.

The porous disintegratable solid substrate can include anionic surfactants, phospholipid surfactants, nonionic surfactants, and combinations thereof. The surfactants may be present from about 1% to about 70%, by weight of the substrate, in an embodiment from about 1% to about 60%, by weight of the substrate, in another embodiment from about 2.5% to about 50%, by weight of the substrate, in a further embodiment from about 2.5% to about 40%, by weight of the substrate, in another embodiment from about 2.5% to about 30%, by weight of the substrate, in another embodiment from about 3% to about 25%, by weight of the substrate, and in another embodiment from about 5% to about 20%, by weight of the substrate.

Anionic Surfactants

Non-limiting examples of anionic surfactants suitable for use herein include lauric acid, docusate sodium, sodium lauryl sulfate, and combinations thereof.

Phospholipid Surfactants

Non-limiting examples of phospholipid surfactants suitable for use herein include lecithin, dilauroyl phosphatidylcholine, dilauroyl phosphatidylcholine, dimyristoyl phosphatidylcholine, dimyristoyl phosphatidylcholine, dipalmitoyl phosphatidylcholine, distearoyl phosphatidylcholine, distearoyl phosphatidylcholine, dioleoyl phosphatidylcholine, dierucoyl phosphatidylcholine, palmitoyloleoyl phosphatidylcholine, dimyristoyl phosphatidylglycerol, dipalmitoyl phosphatidylglycerol, distearoyl phosphatidylglycerol, dioleoyl phosphatidylglycerol, palmitoyloleoyl phosphatidylglycerol, dimyristoyl phosphatidylethanolamine, dipalmitoyl phosphatidylethanolamine, distearoyl phosphatidylethanolamine, distearoyl phosphatidylethanolamine, dioleoyl phosphatidylethanolamine, dimyristoyl phosphatidic acid, dipalmitoyl phosphatidic acid, distearoyl phosphatidic acid, dioleoyl phosphatidylserine, and combinations thereof.

Non-Ionic Surfactants

Suitable nonionic surfactants for use in the personal health care articles of the present invention include, but are not limited to, myristyl alcohol, alpha tocopherol, glyceryl monooleate, macrogol 15 hydroxystearate, polyoxyethylene sorbitan fatty acid esters, polyoxylglycerides, sorbitan esters (Sorbitan Fatty Acid Esters), and combinations thereof.

Non-limiting examples of polyoxyethylene sorbitan fatty acid esters can include Polysorbate 20, Polysorbate 21, Polysorbate 40, Polysorbate 60, Polysorbate 61, Polysorbate 65, Polysorbate 80, Polysorbate 81, Polysorbate 85, Polysorbate 120, and combinations thereof.

Non-limiting examples of polyoxylglycerides can include caprylocaproyl polyoxylglycerides, lauroyl polyoxylglycerides, linoleoyl polyoxylglycerides, oleoyl polyoxylglycerides, stearoyl polyoxylglycerides, and combinations thereof.

Non-limiting examples of sorbitan esters (sorbitan fatty acid esters) can include sorbitan diisostearate, sorbitan dioleate, sorbitan monolaurate, sorbitan monoisostearate, sorbitan monooleate, sorbitan monopalmitate, sorbitan monostearate, sorbitan sesquiisostearate, sorbitan sesquioleate, sorbitan sesquistearate, sorbitan triisostearate, sorbitan trioleate, sorbitan tristearate, and combinations thereof.

Polymer

The porous disintegratable solid substrate may comprise one or more polymers suitable for use in personal health care articles. The one or more polymers may function as a structurant and in certain embodiments may also provide a health benefit.

The one or more polymers may be present from about 10% to about 70% by weight of the substrate, in another embodiment from about 15% to about 50% by weight of the substrate, in another embodiment from about 15% to 40%, by weight of the substrate, and in yet another embodiment from about 20% to about 30%, by weight of the substrate.

Each polymer of the present invention is selected such that its weighted average molecular weight is from about 40,000 Daltons (Da) to about 500,000 Da, in an embodiment from about 50,000 Da to about 400,000 Da, in yet another embodiment from about 60,000 Da to about 300,000 Da, and in still another embodiment from about 70,000 Da to about 200,000 Da. The weighted average molecular weight is computed by summing the average molecular weights of each polymer raw material multiplied by their respective relative weight percentages by weight of the total weight of polymers present within the porous disintegratable solid substrate.

The one or more polymers can include naturally sourced polymers, cellulose derivatives, fiber polymers, carbomers, polymethacrylates, other synthetic polymers, and combinations thereof.

Non-limiting examples of naturally sourced polymers can include alginates, gums, protein based polymers, starch based polymers, native starches, modified starches, other naturally sourced polymers, and combinations thereof. Non-limiting examples of alginates can include ammonium alginate, calcium alginate, potassium alginate, propylene glycol alginate, and combinations thereof. Non-limiting examples of gums can include acacia gum, carrageenan, tragacanth gum, guar gum, locust bean gum, xanthan gum, gellan gum, and combinations thereof. Non-limiting examples of protein based polymers can include whey protein isolate, soy protein isolate, egg albumin, casein, collagen, glutelin, gelatin, gluten, zein, and combinations thereof. Non-limiting examples of starch based polymers can include cereals, tubers, roots, legumes, fruits, and combinations thereof. Non-limiting examples of native starches can include can include waxy or high amylase varieties of corn, pea, potato, banana, barley, wheat, rice, sago, amaranth, tapioca, arrowroot, canna, sorghum, and combinations thereof. Non-limiting examples of modified starches can include hydroxypropyl starch, maltodextrin, high amylose starch, and combinations thereof. Non-limiting examples of other naturally sourced polymers can include agar, pectins, pullulan, citrus fiber, chitin, chitosan, shellac, and combinations thereof.

Non-limiting examples of cellulose derivatives can include hydroxyethylmethyl cellulose, hydroxylpropylmethyl cellulose, hydroxypropyl cellulose, hydroxypropylethyl cellulose, methylcellulose, and combinations thereof.

Non-limiting examples of fiber polymers can include pectins, psyllium, fructo-oligosaccharides, inulin, agar, beta-glucans, chitins, dextrins, lignin, celluloses, non-starch polysaccharides, reduced starch, polycarbophil, and combinations thereof.

Non-limiting examples of carbomers can include carbomer 934, carbomer 934P, carbomer 940, carbomer 94, carbomer 1342, carbomer copolymers, carbomer homopolymers, carbomer interpolymers, and combinations thereof. Some carbomers are available commercially as Carbopol® 934P NF polymer, Carbopol® 971P NF polymer, and Carbopol® 974P NF polymer.

Non-limiting examples of polymethacrylates can include ammonio methacrylate copolymer, basic butylated methacrylate copolymer, methacrylic acid-methyl methacrylate copolymer (1:1), methacrylic acid-ethyl acrylate copolymer (1:1), methacrylic acid-ethyl acrylate copolymer (1:1), methacrylic acid-methyl methacrylate copolymer (1:2), polyacrylate dispersion 30%, methacrylic acid copolymer, amino methacrylate copolymer, ammonio methacrylate copolymer, ammonio methacrylate copolymer dispersion, ethyl acrylate and methyl methacrylate copolymer, and combinations thereof. Some polymethacrylates are available commercially as Eudragit® E 12.5, Eudragit® E 100, Eudragit® E PO, Eudragit® L 12.5 P, Eudragit® L 12.5, Eudragit® L 100, Eudragit® L 100-55, Eudragit® L 30 D-55, Eudragit® S 12.5 P, Eudragit® S 12.5, Eudragit® S 100, Eudragit® FS 30 D, Eudragit® RL 12.5, Eudragit® RL 100, Eudragit® RL PO, Eudragit® RL 30 D, Eudragit® RS 12.5, Eudragit® RS 100, Eudragit® RS PO, Eudragit® RS 30 D, Eudragit® NE 30 D, Eudragit® NE 40 D, Eudragit® NM 30 D, Eastacryl™ 30 D, Kollicoat® MAE 30 DP, Kollicoat® MAE 100 P, Acryl-EZE®, Acryl-EZE® 93 A, and Acryl-EZE® MP.

Non-limiting examples of other synthetic polymers can include polyvinyl alcohol, carbomers, polymethacrylates, carboxyvinyl polymers, polyvinyl alcohols, polyvinyl pyrrolidones, and combinations thereof.

Health Care Active

The porous disintegratable solid substrate may comprise one or more health care actives. The one or more health care actives can include respiratory agents, gastrointestinal agents, central nervous system (CNS) agents, anti-infective agents, nutritional agents, overall wellbeing agents and combinations thereof. The one or more health care actives of the present invention can also be selected from the group consisting of delayed release health care actives, extended release health care actives, immediate release health care actives, and combinations thereof.

The personal health care articles of the present invention may also treat one or more health conditions. Non-limiting examples of health conditions can include respiratory conditions, gastrointestinal conditions, CNS conditions, pathogenic infections, nutritional deficiencies, and combinations thereof.

The personal health care articles of the present invention may also provide one or more health benefits. Non-limiting examples of health benefits can include respiratory benefits, gastrointestinal benefits, CNS benefits, anti-infection benefits, nutritional benefits, overall wellbeing benefits, and combinations thereof.

All health care actives may be present from about 0.025% to about 85%, by weight of said substrate, in an embodiment; in another embodiment from about 0.05% to about 80%; in a different embodiment from about 0.1% to about 75% by weight of said substrate; in another embodiment from about 0.2% to about 70%, by weight of said substrate; in a different embodiment from about 0.3% to about 60%, by weight of said substrate; in another embodiment from about 1% to about 60%, by weight of said substrate; from about 2% to about 50%, by weight of said substrate, in a different embodiment; from about 3% to about 40%, by weight of said substrate, in another embodiment, in a different another embodiment from about 10% to about 40%, by weight of the substrate, and in yet another embodiment from about 10% to about 30%, by weight of the substrate.

Respiratory Agents

In an embodiment one or more health care actives can be a respiratory agent. Non-limiting examples of respiratory agents can include nasal decongestants, mucolytics, expectorants, antihistamines, non-narcotic antitussives, demulcents, anesthetics, plant-derived respiratory agents, and combinations thereof. Respiratory agents may be used to treat respiratory conditions. Non-limiting examples of respiratory conditions can include influenza, the common cold, pneumonia, bronchitis, and other viral infections; pneumonia, bronchitis, and other bacterial infections; allergies; sinusitis; rhinitis; and combinations thereof. Respiratory agents may provide a respiratory benefit. Non-limiting examples of respiratory benefits can include treating, respiratory symptoms. Non-limiting examples of respiratory symptoms include nasal congestion, chest congestion, rhinorrhea, coughing, sneezing, headache, body aches, fever, fatigue or malaise, sore throat, difficulty breathing, sinus pressure, sinus pain, and combinations thereof.

Nasal Decongestants

Non-limiting examples of decongestants can include phenylephrine, 1-desoxyephedrine, ephedrine, propylhexedrine, pseudoephedrine, phenylpropanolamine, and combinations thereof. Decongestants can be present in the porous disintegratable solid substrates from about 0.5% to about 40%, by weight of the substrate, alternatively from about 1% to about 30%, by weight of the substrate, and alternatively from about 5% to about 20%, by weight of the substrate.

Mucolytics

Non-limiting mucolytics can include ambroxol, bromhexine, N-acetylcysteine, and combinations thereof. Mucolytics can be present in the porous disintegratable solid substrates from about 0.5% to about 40%, by weight of the substrate, alternatively from about 1% to about 50%, by weight of the substrate, and alternatively from about 10% to about 60%, by weight of the substrate.

Expectorants

Non-limiting expectorants can include guaifenesin, terpin hydrate, and combinations thereof. Expectorants can be present in the porous disintegratable solid substrates from about 1% to about 40%, by weight of the substrate, alternatively from about 2% to about 50%, by weight of the substrate, and alternatively from about 10% to about 60%, by weight of the substrate.

Antihistamines

Non-limiting examples of antihistamines can include chlorpheniramine, diphenhydramine, doxylamine, triprolidine, clemastine, pheniramine, brompheniramine, dexbrompheniramine, loratadine, cetirizine and fexofenadine, amlexanox, alkylamine derivatives, cromolyn, acrivastine, ibudilast, bamipine, ketotifen, nedocromil, omalizumab, dimethindene, oxatomide, pemirolast, pyrrobutamine, pentigetide, thenaldine, picumast, tolpropamine, ramatroban, repirinast, suplatast tosylate aminoalkylethers, tazanolast, bromodiphenhydramine, tranilast, carbinoxamine, traxanox, chlorphenoxamine, diphenylpyaline, embramine, p-methyl-diphenhydramine, moxastine, orphenadrine, phenyltoloxamine, setastine, ethylenediamine derivatives, chloropyramine, chlorothen, methapyrilene, pyrilamine, talastine, thenyldiamine, thonzylamine hydrochloride, tripelennamine, piperazines, chlorcyclizine, clocinizine, homochlorcyclizine, hydroxyzine, tricyclics, phenothiazines, mequitazine, promethazine, thiazinamium methylsulfate, azatadine, cyproheptadine, deptropine, desloratadine, isothipendyl, olopatadine, rupatadine, antazoline, astemizole, azelastine, bepotastine, clemizole, ebastine, emedastine, epinastine, levocabastine, mebhydroline, mizolastine, phenindamine, terfenadine, tritoqualine, and combinations thereof. Antihistamines can be present in the porous disintegratable solid substrates from about 0.5% to about 30%, by weight of the substrate, alternatively from about 1% to about 20%, by weight of the substrate, alternatively from about 5% to about 15%, by weight of the substrate.

Non-Narcotic Antitussives

Non-limiting examples of antitussives can include benzonatate, chlophedianol, dextromethorphan, levodropropizine, and combinations thereof. Antitussives can be present in the porous disintegratable solid substrates from about 0.5% to about 30%, by weight of the substrate, alternatively from about 1% to about 20%, by weight of the substrate, and alternatively from about 5% to about 15%.

Demulcents

Non-limiting examples of demulcents can include glycerin, honey, pectin, gelatin, slippery elm bark, liquid sugar, glycyrrhizin, and combinations thereof. Demulcents can be present in the porous disintegratable solid substrates from about 1% to about 60%, by weight of the substrate, alternatively from about 5% to about 50%, by weight of the substrate, and alternatively from about 10% to about 40%, by weight of the substrate.

Anesthetics

Non-limiting examples of anesthetics can include menthol, phenol, benzocaine, lidocaine, hexylresorcinol, and combinations thereof. Anesthetics can be present in the porous disintegratable solid substrates from about 0.5% to about 40%, by weight of the substrate, alternatively from about 1% to about 30%, by weight of the substrate, and alternatively from about 5% to about 20%, by weight of the substrate. In certain embodiments, the anesthetics can be present in the porous disintegratable solid substrates from about 0.5% to about 20%, and in another embodiment from about 0.5% to about 10%.

Plant-Derived Respiratory Agents

Non-limiting examples of plant-derived respiratory agents can include *Andrographis* (*Andrographis paniculata*), Garlic (*Allium sativum* L.), *Eleutherococcus senticosus*, a guaiacol component (from oils of cassia (*Cinnamomum aromaticum*), clove (*Syzygium aromaticum, Eugenia aromaticum, Eugenia caryophyllata*), or cinnamon (*Cinnamomum zeylanicum, Cinnamomum verum, Cinnamomum loureiroi, Cinnamomum camphora, Cinnamomum tamala, Cinnamomum burmannii*)), borage seed oil (*Borago officinalis*), sage (*Salvia officinalis, Salvia lavandulaefolia, Salvia lavandulifolia*), *Astragalus* (*Astragalus membraneceus*), Boneset (*Eupatorium perfoliatum*), Chamomile (*Matricaria recutita, Chamaemelum nobile*), Cordyceps (*Cordyceps sinensis*), Echinacea (*Echinacea angustifolia* DC, *Echinacea pallida, Echinacea purpurea*), Elder (*Sambucas nigra* L.), Euphorbia, Ginseng (American ginseng, Asian ginseng, Chinese ginseng, Korean red ginseng, *Panax ginseng: Panax* ssp. Including *P. ginseng* C.C. Meyer, and *P. quinquefolius* L.), Goldenseal (*Hydrastis canadensis* L.), Greater celandine (*Chelidonium majus*), Horseradish (*Armoracia rusticana, Cochlearia armoracia*), Kiwi (*Actinidia deliciosa, Actinidia chinensis*), Maitake mushrooms (*Grifola frondosa*) Mistletoe (*Visvum album* L.), Geranium (*Pelargonium sidoides*), Peppermint/Peppermint oil (*Mentha×peperita* L.), Propolis, Slippery elm (*Ulmus rubra* Muhl, *Ulmus fulva* Michx), Sorrel (*Rumex acetosa* L., *Rumex acetosella* L.), Thyme/Thymus extract (*Thymus vulgaris* L.), Wild indigo (*Baptisia australis*), quercetin (a flavanol), and combinations thereof. Plant derived respiratory agents can be present in the porous disintegratable solid substrates from about 0.5% to about 50%, by weight of the substrate, alternatively from about 1% to about 40%, by weight of the substrate, and alternatively from about 10% to about 30%, by weight of the substrate.

Gastrointestinal Agents

In an embodiment the one or more health care actives can be a gastrointestinal agent. Non-limiting examples of gastrointestinal agents can include anti-diarrheals, lower gastrointestinal agents, laxatives, anti-emetics, antacids, anti-flattulents, $H_2$ receptor antagonists, proton pump inhibitors, lipase inhibitors, rafting agents, probiotics, prebiotics, fiber, enzymes, plant derived gastrointestinal agents, anesthetics, and combinations thereof. Gastrointestinal agents may be used to treat gastrointestinal conditions. Non-limiting examples of gastrointestinal conditions can include, gastroesophogeal reflux disease, gastritis, peptic ulcers, dyspepsia, irritable bowel syndrome, colitis, Crohn's disease, Barrett's esophagus, gastrinoma, diarrhea, indigestion, constipation, obesity, pouchitis, diverticulitis, enteritis, enterocolitis, dysphagia, inflamed hemorrhoids, food poisoning and other bacterial infections, influenza and other viral infections, and combinations thereof. Gastrointestinal agents may provide gastrointestinal benefits. Non-limiting examples of gastrointestinal benefits can include restoring digestive balance, treating gastrointestinal symptoms, and combinations thereof. Non-limiting examples of gastrointestinal symptoms can include diarrhea, constipation, upset stomach, vomiting, sour stomach, cramps, gas, bloating, stomach ache, sore throat, difficulty swallowing, unintentional weight loss, visceral hypersensitivity, feeling of fullness, indigestion, nausea, heartburn, urgency to have a bowel movement, lack of appetite, regurgitation, belching, flatulence, blood in stool, dehydration, and combinations thereof.

Anti-Diarrheals

Non-limiting examples of anti-diarrheals can include loperamide hydrochloride, bismuth subsalicylate, attapulgite, activated charcoal, bentonite, and combinations thereof. The anti-diarrheals can be present in the porous disintegratable solid substrates from about 0.25% to about 60%, by weight of the substrate, alternatively from about 0.1% to about 50%, by weight of the substrate, and alternatively from about 5% to about 40%, by weight of the substrate.

Lower Gastrointestinal Agents

Non-limiting examples of lower gastrointestingal agents can include mesalamine, olsalazine sodium, balsalazide disodium, sulfasalazine, tegaserod maleate, and combinations thereof. Lower gastrointestinal agents can be present in the porous disintegratable solid substrates from about 0.5% to about 60%, by weight of the substrate, alternatively from about 1% to about 50%, by weight of the substrate, and alternatively from about 5% to about 40%, by weight of the substrate.

Laxatives

Non-limiting examples of laxatives can include bisacodyl, cascara sagrada, castor oil, cellulose, modified cellulose, fiber, resistant starch, resistant maltodextrin, psyllium, docusate calcium, docusate sodium, glycerin, lactulose, polycarbophil, psyllium, sennosides, mineral oil, polyethylene glycol 400, and combinations thereof. The laxatives can be present in the porous disintegratable solid substrates from about 0.5% to about 85%, by weight of the substrate, alternatively from about 0.1% to about 50%, by weight of the substrate, and alternatively from about 5% to about 40%, by weight of the substrate.

Anti-Emetics

Non-limiting examples of anti-emetics can include cyclizine, meclizine, buclizine, diphenhydramine, dimenhydrinate, scopolamine, trimethobenzamide, dronabinol, 5-$HT_3$ receptor antagonists, aprepitant, and combinations thereof. Anti-emetics can be present in the porous disintegratable solid substrates from about 0.5% to about 50%, by weight of the substrate, alternatively from about 1% to about 40%, by weight of the substrate, and alternatively from about 5% to about 30%, by weight of the substrate.

Antacids

Non-limiting examples of antacids can include sodium bicarbonate, sodium carbonate, calcium carbonate, magnesium carbonate, magnesium hydroxide, aluminum hydroxide, magaldrate, and combinations thereof. The antacids can be present in the porous disintegratable solid substrates from about 10% to about 60%, by weight of the substrate, alternatively from about 25% to about 50%, by weight of the substrate, and alternatively from about 35% to about 45%, by weight of the substrate.

Anti-Flatulents

Non-limiting examples of anti-flatulents can include simethicone, activated charcoal, lactase, and combinations thereof. The anti-flatulents can be present in the porous disintegratable solid substrates from about 0.5% to about 50%, by weight of the substrate, alternatively from about 1% to about 40%, by weight of the substrate, and alternatively from about 5% to about 30%, by weight of the substrate.

$H_2$ Receptor Antagonists

Non-limiting examples of $H_2$ receptor antagonists can include famotidine, ranitidine, cimetidine, nizatidine, and combinations thereof. The $H_2$ receptor antagonists can be present in the porous disintegratable solid substrates from about 0.5% to about 50%, by weight of the substrate, alternatively from about 1% to about 40%, by weight of the substrate, and alternatively from about 2% to about 30%, by weight of the substrate.

Proton Pump Inhibitors

Non-limiting examples of proton pump inhibitors can include omeprazole, lansoprazole, esomeprazole, pantoprazole, rabeprazole, and combinations thereof. The proton pump inhibitors can be present in the porous disintegratable solid substrates from about 0.5% to about 40%, by weight of the substrate, alternatively from about 0.5% to about 20%, by weight of the substrate, alternatively from about 0.5% to about 10%, by weight of the substrate, and in yet another embodiment from about 0.5% to about 5%, by weight of the substrate.

Lipase Inhibitors

Non-limiting examples of lipase inhibitors can include orlistat. The lipase inhibitor can be present in the porous disintegratable solid substrates from about 0.5% to about 40%, by weight of the substrate, alternatively from about 1% to about 35%, by weight of the substrate, and alternatively from about 2% to about 30%, by weight of the substrate.

Rafting Agents

The porous disinitegratable solid substrates of the present invention may comprise rafting agents. Non-limiting examples of rafting agents can include alginates, pectins, fenugreek, guar gum, xanthan gum, carrageenan gum, locust bean gum, psyllium, and combinations thereof. The rafting agent can be present in the porous disintegratable solid substrates from about 1% to about 60%, by weight of the substrate, alternatively from about 5% to about 50%, by weight of the substrate, and alternatively from about 10% to about 40%, by weight of the substrate.

Probiotics

The porous disintegratable solid substrates of the present invention may comprise probiotics. Non-limiting examples of probiotics can include microogranisms of the genera *Bacillus, Bacteroides, Bifidobacterium, Enterococcus* (e.g., *Enterococcus faecium*), *Lactobacillus, Leuconostoc, Saccharomyces*, and combinations thereof. In another embodiment of the invention, the probiotic is selected from bacteria of the genera *Bifidobacterium, Lactobacillus*, and combinations thereof.

Non-limiting examples of microorganisms can include strains of *Streptococcus lactis, Streptococcus cremoris, Streptococcus diacetylactis, Streptococcus thermophilus, Lactobacillus bulgaricus, Lactobacillus acidophilus* (e.g., *Lactobacillus acidophilus* strain), *Lactobacillus helveticus, Lactobacillus bifidus, Lactobacillus casei, Lactobacillus lactis, Lactobacillus plantarum, Lactobacillus rhamnosus, Lactobacillus delbruekii, Lactobacillus thermophilus, Lactobacillus fermentii, Lactobacillus salivarius, Lactobacillus reuteri, Bifidobacterium longum, Bifidobacterium infantis, Bifidobacterium bifidum, Bifidobacterium animalis, Bifidobacterium pseudolongum, Saccharomyces boulardii, Pediococcus cerevisiae, Lactobacillus salivarius*, and combinations thereof. Probiotics can be present in the porous disintegratable solid substrates from about 0.025% to about 10%, by weight of the substrate, alternatively from about 0.025% to about 5%, by weight of the substrate, alternatively from about 0.025% to about 3%, by weight of the substrate, and in yet another embodiment from about 0.025% to about 1%, by weight of the substrate.

Prebiotics

Non-limiting examples of prebiotics can include beet pulp, carob bean, psyllium, citrus pectin, rice bran, locust bean, fructooligosaccharide, inulin, oligofructose, galactooligosaccharide, citrus pulp, mannanoligosaccharides, arabinogalactan, lactosucrose, glucomannan, lactulose, polydextrose, apple pomace, tomato pomace, carrot pomace, cassia gum, xanthan gum, gum karaya, gum talha, gum arabic, cellulose, hemicellulose, cellulose ethers, lignin, and combinations thereof. Prebiotics can be present in the porous disintegratable solid substrates from about 1% to about 85%, by weight of the substrate, alternatively from about 10% to about 60%, by weight of the substrate, and alternatively from about 20% to about 50%, by weight of the substrate.

Fiber

Non-limiting examples of fibers can include, but are not limited to, pectins, psyllium, guar gum, xanthan gum, alginates, gum arabic, fructo-oligosaccharides, inulin, agar, beta-glucans, chitins, dextrins, lignin, celluloses, non-starch polysaccharides, carrageenan, reduced starch, polycarbophil, and combinations thereof.

In an embodiment, the fiber comprises glucose polymers, preferably those which have branched chains. Among such suitable fibers is one marketed under the tradename "Fibersol2", commercially available from Matsutani Chemical Industry Co., Itami City, Hyogo, Japan.

Other non-limiting examples of suitable fibers can include oligosaccharides, such as inulin and its hydrolysis products commonly known as fructo-oligosaccharides, galacto-oligosaccharides, xylo-oligosaccharides, oligo derivatives of starch, and combinations thereof.

The fiber can be provided in any suitable form. A non-limiting example is in the form of a plant material which contains the fiber. Non-limiting examples of suitable plant materials can include asparagus, artichoke, onion, wheat, chicory, beet pulp, residues of these plant materials, and combinations thereof.

A non-limiting example of a fiber from such a plant material is inulin extract from extract of chicory. Suitable inulin extracts can be obtained from Orafti SA of Belgium under the trademark Raftiline®. Alternatively the fiber can be in the form of a fructo-oligosaccharide which can be obtained from Orafti SA of Belgium under the trademark Raftilose®. Alternatively, an oligo-saccharide can be obtained by hydrolyzing inulin, by enzymatic methods, or by using microorganisms as will be understood by those of skill in the art. Alternatively the fiber can be inulin and/or de-sugared inulin available from Cargill Health & Food Technologies, Wayzata, Minn., USA, or from Cosucra SA, Warcoing, Belgium.

In another embodiment, the fiber can be psyllium, available, which can be obtained from The Procter & Gamble Company, Cincinnati, Ohio, under the trademark Metamucil®.

Fiber can be present in the porous disintegratable solid substrates from about 1% to about 85%, by weight of the substrate, alternatively from about 10% to about 60%, by weight of the substrate, and alternatively from about 20% to about 50%, by weight of the substrate.

Enzymes

The porous disintegratable solid substrates of the present invention can comprise enzymes which can include purified enzymes, partially purified enzymes, extracts containing enzymes, and combinations thereof. Enzymes can be produced synthetically, through genetic modification, or they can be produced naturally by plants, animals, or microorganisms. In some embodiments the enzymes are produced by plants such as peppermint, pineapple, or papaya. In other embodiments the enzymes are produced by fungi such as *Aspergillus, Candida, Saccharomyces*, and *Rhizopus*. In another embodiment the enzymes are produced by an animal such as a pig or bovine. In certain embodiments, the enzymes help support a more complete digestion of food for gastrointestinal health, regularity, and normal bowel function. In other embodiments, the enzymes can provide wellness benefits or health benefits.

Non-limiting examples of enzymes can include, but are not limited to, proteases, amylases, lipases, and combinations thereof.

Other non-limiting examples of enzymes can include bromelain, pepsin, papain, amyloglucosidase, glucoamylase, malt diastase, maltase, lactase, α-galactosidase, β-glucanase, cellusase, hemilase, hemicellulase, cellulase, xylanase, invertase, pectinase, pancreatin, rennet, phytase, pancrelipase, and combinations thereof.

Enzymes can be present in the porous disintegratable solid substrates from about 0.5% to about 85%, by weight of the substrate, alternatively from about 5% to about 70%, by weight of the substrate, and alternatively from about 10% to about 50%, by weight of the substrate. In certain embodiments, enzymes can be present in the porous disintegratable solid substrates from about 0.5% to about 70%, by weight of the substrate, in another embodiment from about 0.5% to about 50%, by weight of the substrate, in a different embodiment from about 0.5% to about 10%, by weight of the substrate.

Plant-Derived Gastrointestinal Agents

Non-limiting examples of plant-derived gastrointestinal agents can include materials from the Ginger family (Zigiberaceae), licorice root (*Glycyrrhizin glabra*), marshmallow root (*Althea officinalis, Althea radix*), chamomile (*Matricariae flos, Chamaemelum nobile*), fennel oil, fennel seed (*Foeniculum vulgare*), caraway oil, caraway seed (*Carum carvi, Carvi fructus, Carvi aetheroleum*), lemon balm (*Melissae folium, Melissa*), horehound herb (*Murrubii herba*), and flaxseed alpha-linoleic acid (*Lini semen*). Plant derived gastrointestinal agents can be present in the porous disintegratable solid substrates from about 0.5% to about 50%, by weight of the substrate, alternatively from about 1% to about 40%, by weight of the substrate, and alternatively from about 10% to about 30%, by weight of the substrate.

CNS Agents

In an embodiment the one or more health care actives can be a central nervous system (CNS) agent. Non-limiting examples of CNS agents can include sleep aids, nonsteroidal anti-inflammatory drugs, salicylates, opioid analgesics, miscellaneous central nervous system stimulants, anti-emetics, and combinations thereof. CNS agents may be used to treat CNS conditions. Non-limiting examples of CNS conditions can include insomnia, restless leg syndrome, narcolepsy, pain, tobacco dependence, depression, attention deficit disorder, attention deficit hyperactivity disorder, and combinations thereof. Non-limiting examples of pain can include headaches, migraines, arthritis, post-operative pain, and combinations thereof. CNS agents may provide CNS benefits. Non-limiting examples of CNS benefits can include increasing alertness, restoring normal circadian rhythm, treating CNS symptoms, and combinations thereof. Non-limiting examples of CNS symptoms can include insomnia, abnormal circadian rhythm, pain, inflammation, fatigue, drowsiness, difficulty concentrating, irritation, vomiting, nausea, and combinations thereof.

Sleep Aids

The porous disintegratable solid substrates of the present invention can comprise sleep aids. Non-limiting examples of sleep aids can include aolpidem, eszopiclone, zaleplon, doxepin, diphenhydramine, doxylamine, melatonin, ramelteon, estazolam, flurazepam hydrochloride, quazepam, temazepam, triazolam, and combinations thereof. Sleep aids can be present in the porous disintegratable solid substrates from about 0.5% to about 10%, by weight of the substrate, alternatively from about 1% to about 10%, by weight of the substrate, and alternatively from about 5% to about 10%, by weight of the substrate. In certain embodiments, sleep aids can be present in the porous disintegratable solid substrates from about 10% to about 60%, by weight of the substrate, in another embodiment from about 10 to about 30%, by weight of the substrate, and in further embodiments from about 10 to about 20%, by weight of the substrate.

Nonsteroidal Anti-Inflammatory Drugs

Non-limiting examples of nonsteroidal anti-inflammatory drugs (NSAIDs) can include celecoxib, diclofenac, etodolac, fenoprofen calcium, ibuprofen, indomethacin, ketoprofen, mefenamic acid, meloxicam, naproxen, tolmetin sodium, indomethacin, and combinations thereof. NSAIDs can be present in the porous disintegratable solid substrates from about 1% to about 60%, by weight of the substrate, alternatively from about 5% to about 50%, by weight of the substrate, and alternatively from about 10% to about 40%, by weight of the substrate.

Salicylates

Non-limiting examples of salicylates can include aspirin, magnesium salicylate, salsalate, diflunisal, and combinations thereof. Salicylates can be present in the porous disintegratable solid substrates from about 1% to about 60%, by weight of the substrate, alternatively from about 5% to about 50%, by weight of the substrate, and alternatively from about 10% to about 40%, by weight of the substrate.

Opioid Analgesics

Non-limiting examples of opioid analgesics can include codeine, hydromorphone hydrochloride, methadone hydrochloride, morphine sulfate, oxycodone hydrochloride, and combinations thereof. Opioid analgesics can be present in the porous disintegratable solid substrates from about 0.5% to about 40%, by weight of the substrate, alternatively from about 0.5% to about 30%, by weight of the substrate, and alternatively from about 1% to about 20%, by weight of the substrate.

Miscellaneous Central Nervous System Stimulants

The porous disintegratable solid substrates of the present invention can comprise miscellaneous central nervous system stimulants. Non-limiting examples of miscellaneous CNS stimulants can include caffeine, nicotine, picrotoxin, pentylenetetrazol, and combinations thereof. Miscellaneous central nervous system stimulants can be present in the porous disintegratable solid substrates from about 0.1% to about 60%, by weight of the substrate, alternatively from about 1% to about 40%, by weight of the substrate, and alternatively from about 5% to about 30%, by weight of the substrate.

Anti-Emetics

Non-limiting examples of anti-emetics can include cyclizine, meclizine, buclizine, diphenhydramine, dimenhydrinate, scopolamine, trimethobenzamide, dronabinol, 5-HT$_3$ receptor antagonists, aprepitant, and combinations thereof. Anti-emetics can be present in the porous disintegratable solid substrates from about 0.5% to about 50%, by weight of the substrate, alternatively from about 1% to about 40%, by weight of the substrate, and alternatively from about 5% to about 30%, by weight of the substrate.

Anti-Infective Agents

In an embodiment the one or more health care actives can be an anti-infective agent. Non-limiting examples of anti-infective agents can include antivirals, antimicrobials, and combinations thereof. Anti-infective agents can be used to treat pathogenic infections. Non-limiting examples of pathogenic infections can include tuberculosis, pneumonia, food poisoning, tetanus, typhoid fever, diphtheria, syphilis, meningitis, sepsis, leprosy, whooping cough, lyme disease, gangrene, urinary tract infections, traveler's diarrhea, methicillin-resistant *Staphylococcus aureus* (MRSA), gonorrhea, scarlet fever, cholera, herpes, hepatitis, human immunodeficiency virus (HIV), influenza, measles, mumps, human papillomavirus, polio virus, giardia, malaria, tapeworm, roundworm, and combinations thereof. Anti-infective agents may provide anti-infective benefits. Non-limiting examples of anti-infective benefits can include treat pathogenic infection symptoms. Non-limiting examples of pathogenic infection symptoms can include fever, inflammation, nausea, vomiting, loss of appetite, abnormal white blood cell count, diarrhea, rash, skin lesions, sore throat, headache, stomach ache, muscle pain, fatigue, cough, chest pain, difficulty breathing, burning during urination, and combinations thereof.

Antivirals

Non-limiting examples of antivirals can include ganciclovir, valganciclovir, acyclovir, famciclovir, valacyclovir, amantadine, ribavirin, rimantidine HCl, oseltamivir phosphate, adefovir dipivoxil, entecavir, and combinations thereof. Antivirals can be present in the porous disintegratable solid substrates from about 0.5% to about 60%, by weight of the substrate, alternatively from about 1% to about 30%, by weight of the substrate, and alternatively from about 5% to about 20%, by weight of the substrate. In certain embodiments, the antivirals can be present in the porous disintegratable solid substrates from about 20% to about 60%, by weight of the substrate, and alternatively from about 30% to about 60%, by weight of the substrate, and in a further embodiment from about 40% to about 60%, by weight of the substrate.

Antimicrobials

Non-limiting examples of antimicrobials can include nitroimidazole antibiotics, tetracyclines, penicillin-based antibiotics such as amoxicillin, cephalosporins, carbopenems, aminoglycosides, macrolide antibiotics, lincosamide antibiotics, 4-quinolones, fluoroquinolones, rifamycins, rifaximi, macrolides, nitrofurantoin, and combinations thereof. Antimicrobials can be present in the porous disintegratable solid substrates from about 1% to about 50%, by weight of the substrate, alternatively from about 5% to about 40%, by weight of the substrate, and alternatively from about 10% to about 30%, by weight of the substrate.

Nutritional Agents

In an embodiment the one or more health care actives can be a nutritional agent. Non-limiting examples of nutritional agents can include vitamins, minerals and electrolytes, fiber, fatty acids, and combinations thereof. Nutritional agents can be used to treat nutritional deficiencies. Non-limiting examples of nutritional deficiencies can include a depressed immune system, birth defects in newborns, heart disease, cancer, Alzheimer's disease, eye diseases, nightblindness, osteoporosis, beriberi, pellagra, scurvy, rickets, low hormone levels, hypertension, and combinations thereof. Nutritional agents may provide a nutritional benefit. Non-limiting examples of nutritional benefits can include disease prevention, lowering cholesterol, increased energy and alertness, preventing aging, restoring digestive balance, and treat nutritional deficiency symptoms and combinations thereof. Non-limiting examples of nutritional deficiency symptoms can include fatigue, muscle weakness, irritability, hair loss, unintentional weight loss, unintentional weight gain, slow wound healing, decreased mental ability, stress, bone fractures, decreased eyesight, decreased rate of wound healing, hyperactivity, dermatitis, muscle cramping, cardiac arrhythmias, depression, and combinations thereof.

Vitamins

Non-limiting examples of vitamins can include vitamin C, vitamin $B_{12}$, vitamin $D_2$ (cholecalciferol), vitamin $D_3$ (ergocalciferol), vitamin A, vitamin $B_1$ (thiamine), vitamin $B_2$ (riboflavin), vitamin $B_3$ (niacin), $B_5$ (pantothenic acid), vitamin $B_6$ (pyridoxine, pyridoxal, or pyridoxamine), vitamin $B_7$ (biotin), vitamin $B_9$ (folic acid), Vitamin $B_{12}$ (cyanocobalmin), vitamin E, and combinations thereof. Vitamins can be present in the porous disintegratable solid substrates from about 1% to about 85%, by weight of the substrate, alternatively from about 5% to about 60%, by weight of the substrate, and alternatively from about 10% to about 50%, by weight of the substrate.

Minerals and Electrolytes

Non-limiting examples of minerals can include zinc, iron, calcium, iodine, copper, magnesium, potassium, selenium, and combinations thereof. Minerals can be present in the porous disintegratable solid substrates from about 1% to about 85%, by weight of the substrate, alternatively from about 5% to about 60%, by weight of the substrate, and alternatively from about 10% to about 50%, by weight of the substrate.

Antioxidants

Non-limiting examples of antioxidants can include, but are not limited to, polyphenols, superfruits, and combinations thereof. Antioxidants can be present in the porous disintegratable solid substrates from about 0.5% to about 50%, by weight of the substrate, alternatively from about 1% to about 40%, by weight of the substrate, and alternatively from about 10% to about 30%, by weight of the substrate.

Non-limiting examples of health care actives containing polyphenols can include tea extract, coffee extract, turmeric extract, grapeseed extract, blueberry extract, and combinations thereof. Nonlimiting examples of superfruits can include açaí, blueberry, cranberry, grape, guarana, mangosteen, noni, pomegranate, seabuckthorn, wolfberry (goji), acerola (Barbados cherry, *Malpighia emarginata, Malpighia glabra*), bayberry (yumberry, *Myrica rubra*), bilberry (*Vaccinium myrtillus*), black raspberry (*Rubus occidentalis*), black chokeberry ("aroma", *Aronia melanocarpa*), blackcurrant (*Ribes nigrum*), camu camu (*Myrciaria dubia*), sour (tart) cherry (*Prunus cerasus*), cupuaçu (*Theobroma grandiflorum*), durian (*Durio kutejensis*), elderberry (*Sambucus canadensis, Sambucus nigra*), red guava (*Psidium guajava*, many species), Indian gooseberry (amalaka, amla, *Phyllanthus emblica*), kiwifruit (*Actinidia deliciosa*), lingonberry (*Vaccinium vitis-idaea*), lychee (*Litchi chinensis*), muscadine grape (*Vitis rotundifolia*), papaya (*Carica papaya*), pomelo (*Citrus maxima*), saskatoon berry (*Amelanchier alnifolia*, Nutt), tamarind (*Tamarindus indica*), wild cherry (*Prunus avium*) and yuzu (*Citrus ichangensis, C. reticulata*) and combinations thereof.

Fatty Acids

Non-limiting examples of fatty acids can include Omega-3 fatty acids, Omega-6 fatty acids, and combinations thereof. Fatty acids can be present in the porous disintegratable solid substrates from about 1% to about 60%, by weight of the substrate, alternatively from about 5% to about 40%, by weight of the substrate, and alternatively from about 5% to about 20%, by weight of the substrate.

Non-limiting examples of Omega-3 fatty acids can include alpha-linolenic acid, Alpha-linolenic acid, stearidonic acid, eicosatrienoic acid, eicosatetraenoic acid, eicosapentaenoic acid, docosapentaenoic acid, docosahexaenoic acid, tetracosapentaenoic acid, tetracosahexaenoic acid, and combinations thereof.

Non-limiting examples of Omega-6 fatty acids can include linoleic acid, gamma-linolenic acid, eicosadienoic acid, dihomo-gamma-linolenic acid, arachidonic acid, docosadienoic acid, adrenic acid, docosapentaenoic acid, and combinations thereof.

Overall Wellbeing Agents

In an embodiment the one or more health care actives can be an overall wellbeing agent. Non-limiting examples of overall wellbeing agents can include energy boosting agents, probiotics, prebiotics, fiber, enzymes, vitamins, minerals and electrolytes, antioxidants, fatty acids, and combinations thereof. Overall wellbeing agents can be used to provide one or more overall wellbeing benefits. Non-limiting examples of overall wellbeing benefits can include improving and/or maintaining respiratory health, gastrointestinal health, immune health, mobility and joint health, cardiovascular health, skin health, oral/dental health, hair health, eye health, reproductive health including menstrual health, ear, nose and throat health, mental health, energy, normal blood glucose levels, muscle strength, and combinations thereof.

Energy Boosting Agents

The porous disintegratable solid substrates of the present invention can comprise energy boosting agents. Energy boosting actives may provide mammals with more energy or a perception of more energy.

Non-limiting examples of energy boosting agents can include, but are not limited to, caffeine, Vitamin B complex, green and black tea, taurine, *rhodiola rosea*, Siberian ginseng (*Eleutherococcus senticosus*), vitamin C, iron, CoQ10, L-carnitine, L-Theanine, vitamin D, guarana (*Paullinia cupana*), magnesium, *Schizandra chinensis*, verba mate (*Ilex paraguariensis*), goji berry/Wolfberry (*Lycium barbarum* and *L. chinense*), quercetin (a plant derived flavonol), amalaki/Indian gooseberry (*Phyllanthus emblica*), açaí (from genus *Euterpe*), maca (*Lepidium meyenii*), ginkgo biloba, glucuronolactone, *panax ginseng* (from species within *Panax*, a genus of 11 species of slow-growing perennial plants with fleshy roots, in the family Araliaceae), *Echinacea* (genus of nine species of herbaceous plants in the Family Asteraceae), rooibos (*Aspalathus linearis*), DHEA, aromas and aromatherapy, noni (*Morinda citrifolia*), mangosteen (*Garcinia mangostana*), selenium, and combinations thereof. Energy boosting agents can be present in the porous disintegratable solid substrates from about 0.5% to about 70%, by weight of the substrate, alternatively from about 1% to about 50%, by weight of the substrate, and alternatively from about 10% to about 40%, by weight of the substrate.

Probiotics

The porous disintegratable solid substrates of the present invention may comprise probiotics. Non-limiting examples of probiotics can include microogranisms of the genera *Bacillus, Bacteroides, Bifidobacterium, Enterococcus* (e.g., *Enterococcus faecium*), *Lactobacillus, Leuconostoc, Saccharomyces*, and combinations thereof. In another embodiment of the invention, the probiotic is selected from bacteria of the genera *Bifidobacterium, Lactobacillus*, and combinations thereof.

Non-limiting examples of microorganisms can include strains of *Streptococcus lactis, Streptococcus cremoris, Streptococcus diacetylactis, Streptococcus thermophilus, Lactobacillus bulgaricus, Lactobacillus acidophilus* (e.g., *Lactobacillus acidophilus* strain), *Lactobacillus helveticus, Lactobacillus bifidus, Lactobacillus casei, Lactobacillus lactis, Lactobacillus plantarum, Lactobacillus rhamnosus, Lactobacillus delbruekii, Lactobacillus thermophilus, Lactobacillus fermentii, Lactobacillus salivarius, Lactobacillus reuteri, Bifidobacterium longum, Bifidobacterium infantis, Bifidobacterium bifidum, Bifidobacterium animalis, Bifidobacterium pseudolongum, Saccharomyces boulardii, Pediococcus cerevisiae, Lactobacillus salivarius*, and combinations thereof. Probiotics can be present in the porous disintegratable solid substrates from about 0.025% to about 10%, by weight of the substrate, alternatively from about 0.025% to about 5%, by weight of the substrate, alternatively from about 0.025% to about 3%, by weight of the substrate, and in yet another embodiment from about 0.025% to about 1%, by weight of the substrate.

Prebiotics

Non-limiting examples of prebiotics can include beet pulp, carob bean, psyllium, citrus pectin, rice bran, locust bean, fructooligosaccharide, inulin, oligofructose, galactooligosaccharide, citrus pulp, mannanoligosaccharides, arabinogalactan, lactosucrose, glucomannan, lactulose, polydextrose, apple pomace, tomato pomace, carrot pomace, cassia gum, xanthan gum, gum karaya, gum talha, gum arabic, cellulose, hemicellulose, cellulose ethers, lignin, and combinations thereof. Prebiotics can be present in the porous disintegratable solid substrates from about 1% to about 85%, by weight of the substrate, alternatively from about 10% to about 60%, by weight of the substrate, and alternatively from about 20% to about 50%, by weight of the substrate.

Fiber

Non-limiting examples of fibers can include, but are not limited to, pectins, psyllium, guar gum, xanthan gum, alginates, gum arabic, fructo-oligosaccharides, inulin, agar, betaglucans, chitins, dextrins, lignin, celluloses, non-starch polysaccharides, carrageenan, reduced starch, polycarbophil, and combinations thereof.

In an embodiment, the fiber comprises glucose polymers, preferably those which have branched chains. Among such suitable fibers is one marketed under the tradename "Fibersol2", commercially available from Matsutani Chemical Industry Co., Itami City, Hyogo, Japan.

Other non-limiting examples of suitable fibers can include oligosaccharides, such as inulin and its hydrolysis products commonly known as fructo-oligosaccharides, galacto-oligosaccharides, xylo-oligosaccharides, oligo derivatives of starch, and combinations thereof.

The fiber can be provided in any suitable form. A non-limiting example is in the form of a plant material which contains the fiber. Non-limiting examples of suitable plant materials can include asparagus, artichoke, onion, wheat, chicory, beet pulp, residues of these plant materials, and combinations thereof.

A non-limiting example of a fiber from such a plant material is inulin extract from extract of chicory. Suitable inulin extracts can be obtained from Orafti SA of Belgium under the trademark Raftiline®. Alternatively the fiber can be in the form of a fructo-oligosaccharide which can be obtained from Orafti SA of Belgium under the trademark Raftilose®. Alternatively, an oligo-saccharide can be obtained by hydrolyzing inulin, by enzymatic methods, or by using microorganisms as will be understood by those of skill in the art. Alternatively the fiber can be inulin and/or de-sugared inulin available from Cargill Health & Food Technologies, Wayzata, Minn., USA, or from Cosucra SA, Warcoing, Belgium.

In another embodiment, the fiber can be psyllium, available, which can be obtained from The Procter & Gamble Company, Cincinnati, Ohio, under the trademark Metamucil®.

Fiber can be present in the porous disintegratable solid substrates from about 1% to about 85%, by weight of the substrate, alternatively from about 10% to about 60%, by weight of the substrate, and alternatively from about 20% to about 50%, by weight of the substrate.

Enzymes

The porous disintegratable solid substrates of the present invention can comprise enzymes which can include purified enzymes, partially purified enzymes, extracts containing enzymes, and combinations thereof. Enzymes can be produced synthetically, through genetic modification, or they can be produced naturally by plants, animals, or microorganisms. In some embodiments the enzymes are produced by plants such as peppermint, pineapple, or papaya. In other embodiments the enzymes are produced by fungi such as Aspergillus, Candida, Saccharomyces, and Rhizopus. In another embodiment the enzymes are produced by an animal such as a pig or bovine. In certain embodiments, the enzymes help support a more complete digestion of food for gastrointestinal health, regularity, and normal bowel function. In other embodiments, the enzymes can provide wellness benefits or health benefits.

Non-limiting examples of enzymes can include, but are not limited to, proteases, amylases, lipases, and combinations thereof.

Other non-limiting examples of enzymes can include bromelain, pepsin, papain, amyloglucosidase, glucoamylase, malt diastase, maltase, lactase, α-galactosidase, β-glucanase, cellusase, hemilase, hemicellulase, cellulase, xylanase, invertase, pectinase, pancreatin, rennet, phytase, pancrelipase, and combinations thereof.

Enzymes can be present in the porous disintegratable solid substrates from about 0.5% to about 85%, by weight of the substrate, alternatively from about 5% to about 70%, by weight of the substrate, and alternatively from about 10% to about 50%, by weight of the substrate. In certain embodiments, enzymes can be present in the porous disintegratable solid substrates from about 0.5% to about 70%, by weight of the substrate, in another embodiment from about 0.5% to about 50%, by weight of the substrate, in a different embodiment from about 0.5% to about 10%, by weight of the substrate.

Vitamins

Non-limiting examples of vitamins can include vitamin C, vitamin $B_{12}$, vitamin $D_2$ (cholecalciferol), vitamin $D_3$ (ergocalciferol), vitamin A, vitamin $B_1$ (thiamine), vitamin $B_2$ (riboflavin), vitamin $B_3$ (niacin), $B_5$ (pantothenic acid), vitamin $B_6$ (pyridoxine, pyridoxal, or pyridoxamine), vitamin $B_7$ (biotin), vitamin $B_9$ (folic acid), Vitamin $B_{12}$ (cyanocobalmin), vitamin E, and combinations thereof. Vitamins can be present in the porous disintegratable solid substrates from about 1% to about 85%, by weight of the substrate, alternatively from about 5% to about 60%, by weight of the substrate, and alternatively from about 10% to about 50%, by weight of the substrate.

Minerals and Electrolytes

Non-limiting examples of minerals can include zinc, iron, calcium, iodine, copper, magnesium, potassium, selenium, and combinations thereof. Minerals can be present in the porous disintegratable solid substrates from about 1% to about 85%, by weight of the substrate, alternatively from about 5% to about 60%, by weight of the substrate, and alternatively from about 10% to about 50%, by weight of the substrate.

Antioxidants

Non-limiting examples of antioxidants can include, but are not limited to, polyphenols, superfruits, and combinations thereof. Antioxidants can be present in the porous disintegratable solid substrates from about 0.5% to about 50%, by weight of the substrate, alternatively from about 1% to about 40%, by weight of the substrate, and alternatively from about 10% to about 30%, by weight of the substrate.

Non-limiting examples of health care actives containing polyphenols can include tea extract, coffee extract, turmeric extract, grapeseed extract, blueberry extract, and combinations thereof. Nonlimiting examples of superfruits can include açaí, blueberry, cranberry, grape, guarana, mangosteen, noni, pomegranate, seabuckthorn, wolfberry (goji), acerola (Barbados cherry, Malpighia emarginata, Malpighia glabra), bayberry (yumberry, Myrica rubra), bilberry (Vaccinium myrtillus), black raspberry (Rubus occidentalis), black chokeberry ("aroma", Aronia melanocarpa), blackcurrant (*Ribes nigrum*), camu camu (*Myrciaria dubia*), sour (tart) cherry (*Prunus cerasus*), cupuaçu (*Theobroma grandiflorum*), durian (*Durio kutejensis*), elderberry (*Sambucus canadensis, Sambucus nigra*), red guava (*Psidium guajava*, many species), Indian gooseberry (amalaka, amla, *Phyllanthus emblica*), kiwifruit (*Actinidia deliciosa*), lingonberry (*Vaccinium vitis-idaea*), lychee (*Litchi chinensis*), muscadine grape (*Vitis rotundifolia*), papaya (*Carica papaya*), pomelo (*Citrus maxima*), saskatoon berry (*Amelanchier alnifolia*, Nutt), tamarind (*Tamarindus indica*), wild cherry (*Prunus avium*) and yuzu (*Citrus ichangensis, C. reticulata*) and combinations thereof.

Fatty Acids

Non-limiting examples of fatty acids can include Omega-3 fatty acids, Omega-6 fatty acids, and combinations thereof. Fatty acids can be present in the porous disintegratable solid substrates from about 1% to about 60%, by weight of the substrate, alternatively from about 5% to about 40%, by weight of the substrate, and alternatively from about 5% to about 20%, by weight of the substrate.

Non-limiting examples of Omega-3 fatty acids can include alpha-linolenic acid, Alpha-linolenic acid, stearidonic acid, eicosatrienoic acid, eicosatetraenoic acid, eicosapentaenoic acid, docosapentaenoic acid, docosahexaenoic acid, tetracosapentaenoic acid, tetracosahexaenoic acid, and combinations thereof.

Non-limiting examples of Omega-6 fatty acids can include linoleic acid, gamma-linolenic acid, eicosadienoic acid, dihomo-gamma-linolenic acid, arachidonic acid, docosadienoic acid, adrenic acid, docosapentaenoic acid, and combinations thereof.

Plasticizer

In an embodiment, the porous disintegratable solid substrate of the present invention can comprise a plasticizer suitable for use in personal health care articles. In an embodiment, the one or more plasticizers may be present from about 0% to about 30%, by weight of substrate; in another embodiment from about 1% to about 28%, by weight of the substrate; in another embodiment from about 3% to about 25%, by weight of the substrate; in another embodiment from about 5% to about 20%, by weight of the substrate; and in a further embodiment, from about 8% to about 15%, by weight of the substrate.

Non-limiting examples of plasticizers can include polyols, polycarboxylic acids, polyesters, other suitable plasticizers, and combinations thereof.

Non-limiting examples of polyols can include glycerin, propylene glycol, polyethylene glycol, sugar alcohols including sorbitol, mannitol, and lactitol; mono di- and oligo-saccharides such as fructose, glucose, sucrose, maltose, lactose, and high fructose corn syrup solids, ascorbic acid, and combinations thereof.

Non-limiting examples of polycarboxylic acids can include citric acid, succinic acid, and combinations thereof.

Non-limiting examples of polyesters can include glycerol triacetate, diethyl phthalate, triethyl citrate, tributyl citrate, acetyl triethyl citrate, acetyl tributyl citrate, and combinations thereof.

Non-limiting examples of other suitable plasticizers of the present invention include, but are not limited to, alkyl and allyl phthalates; lactates (e.g., sodium, ammonium and potassium salts); lactic acid; soluble collagen; modified protein; monosodium L-glutamate; proteins and amino acids such as glutamic acid, aspartic acid, and lysine; hydrogen starch hydrolysates; other low molecular weight esters (e.g., esters of C2-C10 alcohols and acids); and any other plasticizer known to one skilled in the art of the food, dietary supplements, and pharmaceutical industries; and combinations thereof.

Aesthetic Agents

The porous disintegratable solid substrate may comprise one or more aesthetic agents. The one or more aesthetic agents can be selected from the group consisting of flavors, colorants, sensates, sweeteners, salivation agents, and combinations thereof. All aesthetic agents can be present from about 0.001% to about 80%, by weight of the substrate, in another embodiment from about 0.005% to about 60%, by weight of the substrate, in still another embodiment from about 0.05% to about 55%, by weight of the substrate, and in another embodiment from about 0.1% to about 50%, by weight of the substrate.

Flavors

The porous disintegratable solid substrate can include one or more flavors. Non-limiting examples of flavors that can be used in the present invention can include natural flavoring agents, artificial flavoring agents, artificial extracts, natural extracts and combination thereof. Non-limiting examples of flavors can include vanilla, honey, lemon, lemon honey, cherry vanilla, peach, honey ginger, chamomile, cherry, cherry cream, mint, vanilla mint, dark berry, black berry, raspberry, peppermint, spearmint, honey peach, acai berry, cranberry, honey cranberry, tropical fruit, dragon fruit, wolf berry, red stem mint, pomegranate, black current, strawberry, lemon, lime, peach ginger, orange, orange cream, cream sickle, apricot, anethole, ginger, jack fruit, star fruit, blueberry, fruit punch, lemon grass, chamomile lemon grass, lavender, banana, strawberry banana, grape, blue raspberry, lemon lime, coffee, espresso, cappuccino, honey, wintergreen mint, bubble gum, tart honey lemon, sour lemon, green apple, boysenberry, rhubarb, strawberry rhubarb, persimmon, green tea, black tea, red tea, white tea, honey lime, cherry lime, apple, tangerine, grapefruit, kiwi, pear, vanillin, ethyl vanillin, maltol, ethyl-maltol, pumpkin, carrot cake, white chocolate raspberry, chocolate, white chocolate, milk chocolate, dark chocolate, chocolate marshmallow, apple pie, cinnamon, hazelnut, almond, cream, crème brûlée, caramel, caramel nut, butter, butter toffee, caramel toffee, aloe vera, whiskey, rum, cocoa, licorice, pineapple, guava, melon, watermelon, elder berry, mouth cooler, raspberries and cream, peach mango, tropical, cool berry, lemon ice, nectar, spicy nectar, tropical mango, apple butter, peanut butter, tangerine, tangerine lime, marshmallow, cotton candy, apple cider, orange chocolate, adipic acid, citral, denatonium benzoate, ethyl acetate, ethyl lactate, ethyl maltol, ethylcellulose, fumaric acid, leucine, malic acid, menthol, methionine, monosodium glutamate, sodium acetate, sodium lactate, tartaric acid, thymol, and combinations thereof. Flavors can be present from about 0.05% to about 5%, by weight of the substrate, in another embodiment from about 0.01% to about 3%, by weight of the substrate, in still another embodiment from about 0.2% to about 2%, by weight of the substrate, and in another embodiment from about 0.1% to about 1.5%, by weight of the substrate.

Colorants

The porous disintegratable solid substrate can include one or more colorants. Non-limiting examples colorants that may be used in the present invention include FD&C blue #1, FD&C blue #2, D&C blue #4, D&C blue #9, FD&C green #3, D&C green #5, D&C green #6, D&C green #8, D&C orange #4, D&C orange #5, D&C orange #10, D&C orange #11, FD&C red #3, FD&C red #4, D&C red #6, D&C red #7, D&C red #17, D&C red #21, D&C red #22, D&C red #27, D&C red #28, D&C red #30, D&C red #31, D&C red #33, D&C red

34, D&C red #36, D&C red #39, FD&C red #40, D&C violet #2, FD&C yellow #5, FD&C yellow #6, D&C yellow #7, Ext. D&C yellow #7, D&C yellow #8, D&C yellow #10, D&C yellow #11, and combinations thereof. Colorants can be present from about 0.05% to about 2%, by weight of the substrate, in another embodiment from about 0.01% to about 2%, by weight of the substrate, and in still another embodiment from about 0.02% to about 1.5%, by weight of the substrate.

Sensantes

The porous disintegratable solid substrate can include one or more sensantes. Non-limiting examples of sensates can include cooling sensates, warming sensates, tingling sensates, and combinations thereof. Sensate are useful to deliver signals to the consumer.

Non-limiting examples of cooling sensates can include WS-23 (2-Isopropyl-N,2,3-trimethylbutyramide), WS-3 (N-Ethyl-p-menthane-3-carboxamide), WS-30 (1-glyceryl-p-menthane-3-carboxylate), WS-4 (ethyleneglycol-p-methane-3-carboxylate), WS-14 (N-t-butyl-p-menthane-3-carboxamide), WS-12 (N-(4-,ethoxyphenyl)-p-menthane-3-carboxamide), WS-5 (Ethyl-3-(p-menthane-3-carboxamido) acetate, Menthone glycerol ketal (sold as Frescolat® MGA by Haarmann & Reimer), (−)-Menthyl lactate (sold as Frescolat® ML by Haarmann & Reimer), (−)-Menthoxypropane-1,2-diol (sold as Coolant Agent 10 by Takasago International), 3-(1-menthoxy)propane-1,2-diol, 3-(1-Menthoxy)-2-methylpropane-1,2-diol, (−)-Isopulegol is sold under the name "Coolact P® " by Takasago International, cis & trans p-Menthane-3,8-diols (PMD38)—Takasago International, Questice® (menthyl pyrrolidone carboxylate), (1R,3R,4S)-3-menthyl-3,6-dioxaheptanoate—Firmenich, (1R,2S,5R)-3-menthyl methoxyacetate—Firmenich, (1R,2S,5R)-3-menthyl 3,6,9-trioxadecanoate—Firmenich, (1R,2S,5R)-menthyl 11-hydroxy-3,6,9-trioxaundecanoate—Firmenich, (1R,2S,5R)-3-menthyl (2-hydroxyethoxy)acetate—Firmenich, Cubebol—Firmenich, Icilin also known as AG-3-5, chemical name 1-[2-hydroxyphenyl]-4-[2-nitrophenyl-]-1,2,3,6-tetrahydropyrimidine-2-one), 4-methyl-3-(1-pyrrolidinyl)-2[5H]-furanone, Frescolat ML—menthyl lactate, Frescolat MGA—menthone glycerin acetal, Peppermint oil, Givaudan 180, L-Monomenthyl succinate, L-monomenthyl glutarate, 3-1-menthoxypropane-1,2-diol—(Coolact 10), 2-1-menthoxyethanol (Cooltact 5), TK10 Coolact (3-1-Menthoxy propane-1,2-diol), Evercool 180 (N-p-benzeneacetonitrile-menthane carboxamide), and combinations thereof. Cooling sensates can be present from about 0.005% to about 10%, by weight of the substrate, in another embodiment from about 0.05% to about 7%, by weight of the substrate, and in still another embodiment from about 0.01% to about 5%, by weight of the substrate.

Non-limiting examples of warming sensates can include TK 1000, TK 1 MM, Heatenol—Sensient Flavors, Optaheat—Symrise Flavors, Cinnamon, Polyethylene glycol, Capsicum, Capsaicin, Curry, FSI Flavors, Isobutavan, Ethanol, Glycerin, Nonivamide 60162807, Hotact VEE, Hotact 1MM, piperine, optaheat 295 832, optaheat 204 656, optaheat 200 349, and combinations thereof. Warming sensates can be present from about 0.005% to about 10%, by weight of the substrate, in another embodiment from about 0.05% to about 7%, by weight of the substrate, and in still another embodiment from about 0.01% to about 5%, by weight of the substrate.

Non-limiting examples of tingling sensates can include sichuan pepper, hydroxy alpha sanshool, citric acid, Jambu extracts, spilanthol, and combinations thereof. Tingling sensates can be present from about 0.005% to about 10%, by weight of the substrate, in another embodiment from about 0.01% to about 7%, by weight of the substrate, and in still another embodiment from about 0.015% to about 6%, by weight of the substrate.

Sweeteners

The porous disintegratable solid substrates can include one or more sweeteners. Sweeteners can be natural or artificial. Non-limiting examples of sweeteners can include nutritive sweeteners, sugar alcohols, synthetic sweeteners, high intensity natural sweeteners, and combinations thereof. All sweeteners can be present from about 0.05% to about 60%, by weight of the substrate, in another embodiment from about 0.1% to about 50%, by weight of the substrate, in yet another embodiment from about 1% to about 10%, by weight of the substrate.

Non-limiting examples of nutritive sweeteners can include sucrose, dextrose, glucose, fructose, lactose, tagatose, maltose, trehalose, and combinations thereof. Nutritive sweeteners can be present from about 0.1% to about 60%, by weight of the substrate, in another embodiment from about 1% to about 50%, by weight of the substrate, and in a further embodiment from about 0.1% to about 10%, by weight of the substrate.

Non-limiting examples of sugar alcohols can include xylitol, sorbiotl, mannitol, maltitol, lactitol, isomalt, erthritol, and combinations thereof. Sugar alcohols can be present from about 0.1% to about 60%, by weight of the substrate, in another embodiment from about 0.11% to about 50%, by weight of the substrate, and in a further embodiment from about 0.1% to about 10%, by weight of the substrate.

Non-limiting examples of synthetic sweeteners can include aspartame, acesulfame potassium, alitame, sodium saccharin, sucralose, neotame, cyclamate, and combinations thereof. Synthetic sweeteners can be present from about 0.05% to about 10% by weight of the substrate, in another embodiment from about 0.1% to about 5%, by weight of the substrate, and in a further embodiment from about 0.25% to about 4%, by weight of the substrate.

Non-limiting examples of high intensity natural sweeteners can include neohesperidin dihydrochalcone, stevioside, rebaudioside A, rebaudioside C, dulcoside, monoammonium glycrrhizinate, thaumatin, and combinations thereof. High intensity natural sweeteners can be present from about 0.05% to about 10% by weight of the substrate, in another embodiment from about 0.1% to about 5%, by weight of the substrate, and in a further embodiment from about 0.25% to about 4%, by weight of the substrate.

Salivation Agents

The porous disintegratable solid substrate can include one or more salivation agents. Non-limiting examples of salivating agents include formula (I):

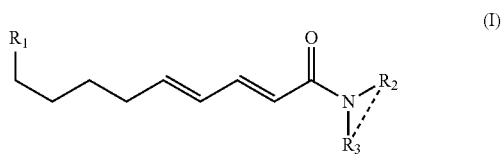

wherein $R_1$ represents C1-C2 n-alkyl; $R_2$ is 2-methyl-1-propyl and $R_3$ is hydrogen, or $R_2$ and $R_3$ taken together is a moiety having the formula $—(CH_2)_n—$ wherein n is 4 or 5, and combinations thereof.

In an embodiment, the salivating agent comprises a material wherein $R_2$ is 2-methyl-1-propyl and $R_3$ is hydrogen, more preferably wherein $R_1$ is C1 n-alkyl, $R_2$ is 2-methyl-1-propyl and $R_3$ is hydrogen. More preferably, the salivating agent comprises trans-pellitorin, a chemical having a structure according to formula (II):

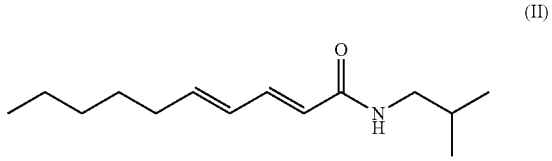 [SMILES: CCCCC/C=C/C=C/C(=O)NCC(C)C]

(II)

In another embodiment, the salivation agent could include sodium bicarbonate, sodium chloride, trans pelitorin, and combinations thereof. Salivation agents can be present from about 0.005% to about 10%, by weight of the substrate, in another embodiment from about 0.01% to about 7%, by weight of the substrate, and in still another embodiment from about 0.015% to about 6%, by weight of the substrate.

Surface Resident Coating

The health care active(s) and/or aesthetic agent(s) can be present as a surface resident coating. In certain embodiments, the surface resident coating covers an outer surface of the personal health care article, putting the surface resident coating in position to immediately contact saliva during use for the release of the health care active(s) and/or aesthetic agent(s). Alternatively, the surface resident coating can be included (e.g., sandwiched or encased) within the personal health care article or between porous disintegratable solid substrates.

In an embodiment the weight ratio of the weight of the porous disintegratable solid substrate to the weight of the surface resident coating is from about 110:1 to about 0.1:1, in another embodiment from about 20:1 to about 0.2:1, and in another embodiment from about 10:1 to about 0.3:1, and in yet another embodiment from about 1:1 to about 0.4:1.

In an embodiment, the amount of surface resident coating can be from about 0.05% to about 70%, by weight of the substrate, in another embodiment from about 1% to about 60%, by weight of the substrate, in a further embodiment from about 5% to about 50%, by weight of the substrate, in a different embodiment from about 10% to about 40%, by weight of the substrate. In certain embodiments, the amount of surface resident coating can be from about 0.05% to about 15%, by weight of the substrate, in another embodiment from about 1% to about 12%, by weight of the substrate, and in a further embodiment from about 2% to about 10%, by weight of the substrate.

In an embodiment the surface resident coating of the present invention may comprise one or more health care actives as defined herein. In another embodiment, the surface resident coating of the present invention may comprise one or more aesthetic agents as defined herein. Those of skill in the art will understand that the porous disintegratable solid substrate can also include one or more health care actives and/or aesthetic agents that are blended or otherwise combined together within a single surface resident coating or that may be applied via a multiplicity of different surface resident coatings that may or may not be in contact with one another (applied as layers or to differing regions of the substrate and combinations thereof) and wherein each surface resident coating may comprise the same or a different health care actives and/or aesthetic agents and the same or different physical form than the other surface resident coatings.

In an embodiment, the porous disintegratable solid substrate may comprise one or more health care actives which can be the same or different from the health care active present in the surface resident coating. In another embodiment, the porous disintegratable solid substrate may comprise one or more aesthetic agents which can be the same or different from the aesthetic agent in the surface resident coating.

The surface resident coating of the present invention may be applied to the porous disintegratable solid substrate or the personal health care article. The surface resident coating can be applied by spraying, dusting, sprinkling, coating, surface-printing (e.g., in the shape of a desired adornment, decoration, or pattern), pouring on, injecting into the interior, dipping, or by any other suitable means, such as by use of a depositor, sifter, or powder bed. In an embodiment, the surface resident coating can be applied as a powder coating or can be a fluid coating. The surface resident coating can be applied over portions or entire regions of the article's exterior surface, and can be applied in a manner to adorn, decorate, form a logo, design, etc.

In certain embodiments, the personal health care article contains a surface resident coating that can be situated below the surface of the porous disintegratable solid substrate. For instance, the porous disintegratable solid substrate could contain dimples and the surface resident coating could be located within the dimples of the substrate. In another embodiments, the surface resident coating may permeate the porous disintegratable solid substrate in whole or in part.

In another embodiment, the personal health care article comprises a first porous disintegratable solid substrate and a second porous disintegratable solid substrate, and the surface resident coating is situated between the first porous disintegratable solid substrate and the second porous disintegratable solid substrate. In this embodiment, the two porous disintegratable solid substrates can be joined together (e.g., via sealing the adjoining surfaces or edges with a thin layer of water and/or plasticizer so as to not substantially dissolve the substrate and applied pressure to induce adhesion). Alternatively, in certain embodiments, the surface resident coating may be on one porous disintegratable solid substrate which is folded over to form a pouch, encasing the powder. In another embodiment, the porous disintegratable solid substrate is at least partially coated with a first surface resident coating and a second surface resident coating, wherein the multiple surface resident coatings can be applied to separate areas of the substrate, such as separate sides of the substrate, or the multiple surface resident coatings can be applied one over the other.

Process for Manufacture

An embodiment is directed to a process of making a personal health care article comprising the steps of: (a) preparing a mixture comprising from about 1% to about 70% of a surfactant, from about 10% to about 70% of one or more polymers, and from about 0.025% to about 85% of one or more health care actives; (b) introducing a gas into said mixture to form a wet aerated mixture; (c) shaping said wet aerated mixture into at least one shaped wet mixture; (d) drying at least one shaped wet mixture; and (e) forming a porous disintegratable solid substrate having a final moisture content of from about 0.5% to about 15% moisture.

An additional embodiment relates to a process of making a personal health care article comprising the steps of: (a) preparing a mixture comprising from about 1% to about 70% of a surfactant and from about 10% to about 70% of one or more polymers; (b) introducing a gas into said mixture to form a wet aerated mixture; (c) shaping said wet aerated mixture into at least one shaped wet mixture; (d) drying at least one shaped wet mixture; and (e) forming a porous disintegratable solid substrate having a final moisture content of from about 0.5% to about 15% moisture; and (f) applying a surface resident coating comprising one or more health care actives to said porous disintegratable solid substrate.

Preparing the Mixture

The mixture may be prepared by combining the polymer in the presence of water, surfactant and other optional ingredients. The other ingredients may include one or more health care actives, one or more aesthetic agents, a plasticizer, and combinations thereof. This can be accomplished by any suitable mixing system. Any process can be envisioned such that the polymer, surfactant, and other ingredients are sufficiently combined in the presence of water. In certain embodiments, the polymer completely dissolves in the solution.

The mixture of the present invention can have a viscosity of from about 2,500 cps to about 150,000 cps, in an embodiment from about 5,000 cps to about 100,000 cps, in another embodiment from about 7,500 cps to about 75,000 cps, and in still another embodiment from about 10,000 cps to about 60,000 cps. The processing mixture viscosity values are measured using a TA Instruments AR500 Rheometer with 4.0 cm diameter parallel plate and 1,200 micron gap at a shear rate of 1.0 reciprocal seconds for a period of 30 seconds at 23° C.

Introducing a Gas

A gas can be introduced into the mixture to form a wet aerated mixture. Non-limiting examples of gases that can be introduced include air, helium, argon, neon, krypton, xenon, sulfur hexafluoride, and mixtures thereof.

In an embodiment the gas is introduced by mechanical mixing energy. In another embodiment this may be achieved via chemical means. The introduction of the gas may be accomplished by any suitable mechanical processing means, including but not limited to: (i) Batch tank aeration via mechanical mixing including planetary mixers or other suitable mixing vessels, (ii) semi-continuous or continuous aerators utilized in the food industry (pressurized and non-pressurized), or (iii) spray-drying the mixture in order to form aerated beads or particles that can be compressed such as in a mold with heat in order to form the wet aerated mixture.

In another embodiment, it has been discovered that the gas can be introduced within continuous pressurized aerators that are conventionally utilized within the food industry in the production of marshmallows. Suitable continuous pressurized aerators include the Morton whisk (Morton Machine Co., Motherwell, Scotland), the Oakes continuous automatic mixer (E.T. Oakes Corporation, Hauppauge, N.Y.), the Fedco Continuous Mixer (The Peerless Group, Sidney, Ohio), and the Preswhip (Hosokawa Micron Group, Osaka, Japan).

In another embodiment, the gas can be introduced with a KitchenAid® Mixer (available from Hobart Corporation, Troy, Ohio) fitted with a flat beater attachment. The KitchenAid® can be used at high speed to aerate the mixture. In yet another embodiment, the gas can be introduced with chemical foaming agents by in-situ gas formation (via chemical reaction of one or more ingredients, including formation of carbon dioxide ($CO_2$ (g)) by an effervescent system.

In an embodiment the wet density range of the wet aerated mixture range from about 0.10 $g/cm^3$ to about 0.50 $g/cm^3$, in another embodiment from about 0.15 $g/cm^3$ to about 0.45 $g/cm^3$, in another embodiment from about 0.20 $g/cm^3$ to about 0.40 $g/cm^3$, and in yet another embodiment from about 0.25 $g/cm^3$ to about 0.35 $g/cm^3$, as measured by the Wet Density Method described hereafter.

Forming the Shaped Wet Mixture

The forming of the shaped wet mixture may be accomplished by any suitable means to form the wet aerated mixture in a desired shape or shapes including, but not limited to (i) depositing the wet aerated mixture to molds of the desired shape and size comprising a non-interacting and non-stick surface including aluminium, Teflon, metal, HDPE, polycarbonate, neoprene, rubber, LDPE, glass and the like; (ii) depositing the wet aerated mixture into cavities imprinted in dry granular starch contained in a shallow tray, otherwise known as starch moulding forming technique; and (iii) depositing the wet aerated mixture onto a continuous belt or screen comprising any non-interacting or non-stick material Teflon, metal, HDPE, polycarbonate, neoprene, rubber, LDPE, glass and the like which may be later stamped, cut, embossed or stored on a roll.

Drying the Shaped Wet Mixture

The drying of at least one shaped wet mixture may be accomplished by any suitable means including, but not limited to (i) drying room(s) including rooms with controlled temperature and pressure or atmospheric conditions; (ii) ovens including non-convection or convection ovens with controlled temperature and optionally humidity; (iii) truck/tray driers, (iv) multi-stage inline driers; (v) impingement ovens; (vi) rotary ovens/driers; (vii) inline roasters; (viii) rapid high heat transfer ovens and driers; (ix) dual plenum roasters, and (x) conveyor driers, and combinations thereof. Any suitable drying means that does not compromise the final structure of the porous disintegratable solid substrate can be used. However, a drying method that compromises the final structure of the porous disintegratable solid structure, such as freeze drying, is preferably not used.

In an embodiment, the drying environment is heated to a temperature between 20° C. and 150° C., in another embodiment between 40° C. and 145° C., in a further embodiment, the drying temperature is between 75° C. and 145° C., in another embodiment, the drying temperature is between 100° C. and 140° C., and in yet another embodiment the drying temperature is between 115° C. and 135° C.

In an embodiment, the drying time to achieve the desired moisture content of the porous disintegratable solid substrate is from about 3 minutes to about 24 hours, in another embodiment from about 3 minutes to about 18 hours, in another embodiment from about 3 minutes to about 14 hours, in a further embodiment from about 3 minutes to about 12 hours, in another embodiment from about 3 minutes to about 90 minutes, in another embodiment from about 5 minutes to about 60 minutes, in another embodiment from about 7 minutes to about 45 minutes.

In another embodiment, the shaped wet mixture can be dried using Microwave drying. Microwave drying may be achieved via a low energy density applicator such as those commercially available from Industrial Microwave Systems L.L.C Morrisville, N.C. (http://www.industrialmicrowave.com). In some embodiments, a low energy two wide wave applicators in series microwave applicator system is preferred with two or more low energy applicator regions (about 5 kW). The air environment within the low energy microwave applicator system can from about 35° C. to about 90° C. in one embodiment and from about 40° C. to about 70° C. in another embodiment. The drying times that can be achieved via Microwave drying are between about 3 minutes and about 25 minutes, in another embodiment between about 5 minutes and about 20 minutes, and in another embodiment between about 7 minutes and about 15 minutes.

In another embodiment, each shaped wet mixture is placed into a convection oven for drying. The drying time for drying in a convection oven with a temperature between about 40° C. and about 50° C. is from about 14 hours to about 18 hours. The drying time for drying in a convection oven with a temperature between about 120° C. and about 140° C. is from about 5 minutes to about 60 minutes.

Other suitable drying environments include "volumetric heating" techniques using high frequency electromagnetic fields such as Microwave Drying and Radio Frequency (RF) Drying. With these techniques, the energy is transferred electromagnetically through the shaped wet mixture rather than by conduction or convection.

The shaped wet mixture is dried until it has the desired final moisture content. In one embodiment, the shaped wet mixture is dried to a moisture content of from about 0.5% to about 15%, in one embodiment from about 3% to about 15%, in another embodiment from about 5% to about 15% and in yet another embodiment from about 7% to about 15%.

Applying the Surface Resident Coating

Applying a surface resident coating comprising one or more health care actives and/or one or more aesthetic agents may include any suitable mechanical, chemical, or otherwise means to produce a particulate surface resident coating comprising the health care actives or aesthetic agents.

The surface resident coating can be applied by spraying, dusting, sprinkling, coating, surface-printing (e.g., in the shape of a desired adornment, decoration, or pattern), pouring on, injecting into the interior, dipping, or by any other suitable means, such as by use of a depositor, sifter, or powder bed. The surface resident coating can be applied over portions or entire regions of the porous disintegratable solid substrate or personal health care article, and can be applied in a manner to adorn, decorate, form a logo, design, etc.

When the surface resident coatings are applied to the porous disintegratable solid substrate or personal health care article as a fluid the fluid can be applied as a spray, a gel, or a cream coating.

When the surface resident coatings are a powder, the powder can be applied by allowing the porous disintegratable solid substrate to have a tacky surface by drying the shaped wet mixture to a specific moisture content before applying the powder to facilitate the adherence of the surface resident coating. In another embodiment, a surface of the porous disintegratable substrate is brushed with a cotton swab dipped in distilled water and then the powder can be applied. In another embodiment, the porous disintegratable solid substrate or personal health care article is placed in a bag, tray, belt, or drum containing or otherwise exposed to the powder and agitated, rolled, brushed, vibrated or shaken to apply and distribute the powder, either in a batch or continuous production manner. Other powder application methods may include powder sifters, electrostatic coating, tribo charging, fluidized beds, powder coating guns, corona guns, tumblers, electrostatic fluidized beds, electrostatic magnetic brushes, and/or powder spray booths.

Test Methods

Disintegration Rate Method

The personal health care article of the present invention can have a disintegration rate that allows the personal health care article to disintegrate when exposed to water or saliva. In one example, the disintegration rate of the personal health care article can be less than about 180 seconds, in another example less than about 120 seconds, in another example less than 90 seconds, in another example less than about 60 seconds, in another example less than 45 seconds, in another example less than 38 seconds, in another example less than about 30 seconds, in another example less than about 15 seconds, and in another example less than about 10 seconds. The disintegration rate can be evaluated according to USP General Chapter <701> using artificial saliva or water as the disintegration medium. For example, one suitable apparatus is the Vankel VK100 (Agilent Technologies) Disintegration Apparatus. An example of suitable conditions includes using water at 37.6° C. and fluted disk sinkers to avoid floating of the health care article.

Dissolution Rate Method

The personal health care article of the present invention can have a dissolution rate that allows the personal health care article to dissolve when exposed to water, saliva or gastric fluid. In one example, for a personal health care article comprising an immediate release active can reach 85% dissolution of the health care active within less than about 15 minutes, in another example less than about 10 minutes, in another example less than about 5 minutes, in another example less than about 3 minutes, and in another example less than about 1 minute. The dissolution rate of the health care article can be evaluated using USP Apparatus 1 at 100 rpm using artificial saliva, water, or simulated gastric fluid as the dissolution medium (USP General Chapter <711>). Analysis of the dissolved quantity of health care active(s) in the media at various time points can be conducted using the appropriate USP monograph methods for the specific active(s).

Thickness Method

The thickness of the personal health care article or the porous disintegratable solid substrate is taken as the maximum distance in the shortest direction and is measured in millimeters (mm). The thickness is calculated as the length obtained using a micrometer or thickness gage, such as the Mitutoyo Corporation Digital Disk Stand Micrometer Model Number IDS-1012E (Mitutoyo Corporation, 965 Corporate Blvd, Aurora, Ill., USA 60504). The micrometer has a 1 inch diameter platen weighing about 32 grams (g), which measures thickness at an application pressure of about 0.009 psi (6.32 gm/cm2).

The thickness of the personal health care article or the porous disintegratable solid substrate is measured by raising the platen, placing a section of the sample on the stand beneath the platen, carefully lowering the platen to contact the sample, releasing the platen, and measuring the thickness of the sample in millimeters on the digital readout. The sample should be fully extended to all edges of the platen to make sure thickness is measured at the lowest possible surface pressure, except for the case of more rigid samples which are not flat. For more rigid samples which are not completely flat, a flat edge of the sample is measured using only one portion of the platen impinging on the flat portion of the sample. In the case of cylindrical, spherical, or other objects with more of a third dimension versus a pad or strip, the thickness is taken as the maximum distance of the shortest dimension, i.e., the diameter of a sphere or cylinder for instance, and the thickness ranges are the same as described above.

Basis Weight Method

The Basis Weight of the personal health care article and the porous disintegratable solid substrate is calculated as the weight of the article or substrate per area of the article or substrate (grams/meter$^2$). The weight and area measurements are made after the wet aerated mixture is dried and the porous disintegratable solid substrate has been at the desired moisture content for one hour. The area is calculated as the projected area onto a flat surface perpendicular to the outer edges of the personal health care article or the porous disintegratable solid substrate. For a flat object, the area is thus computed based on the area enclosed within the outer perimeter of the sample. For a spherical object, the area is thus computed based on the average diameter as $3.14 \times (diameter/2)^2$. For a cylindrical object, the area is thus computed based on the average diameter and average length as diameter×length. For an irregularly shaped three dimensional object, the area is computed based on the side with the largest outer dimensions projected onto a flat surface oriented perpendicularly to this side.

Cell Wall Thickness Method

The Cell Wall Thickness of the personal health care article and the porous disintegratable solid substrate is computed from the scanned images via a micro computed tomography system (µCT80, SN 06071200, Scanco Medical AG) as described herein. The Cell Wall Thickness is determined according to the method defined for the measurement of Trabecular Thickness using Scanco Medical's Bone Trabecular Morphometry evaluation. The definition of Trabecular Thickness as taken from the Scanco User's manual: Trabecular Thickness uses a Euclidean distance transformation (EDM), which calculates the Euclidean distance from any point in the foreground to the nearest background point. The Trabecular Thickness measure represents twice the centerline values associated with the local maxima of the EDM, which represents the distance to the center of the object (twice this distance will yield the thickness). The cell wall thickness is measured in millimeters (mm).

Cell Inter-Connectivity

The personal health care article and the porous disintegratable solid substrate of the present invention can have a high degree of cell inter-connectivity, i.e., are predominantly open-celled porous disintegratable solid substrates as opposed to being predominantly closed-cell solid foams. The cell inter-connectivity can be assessed by the Structure Model Index, the Star Volume Method, and the Gas Pycnometry Method.

Structure Model Index Method

Cell interconnectivity can be determined via the Structure Model Index (SMI). Disk-like samples, approximately 4 cm in diameter and 3 to 7 mm high, are scanned using a micro computed tomography system (µCT80, SN 06071200, Scanco Medical AG). Each sample is imaged while sitting flat on the bottom of a cylindrical tube. Image acquisition parameters are 45 kVp, 177 µA, 51.2 mm field of view, 800 ms integration time, 1000 projections. The number of slices is adjusted to cover the height of the sample. The reconstructed data set consisted of a stack of images, each 2048×2048 pixels, with an isotropic resolution of 25 µm. For data analysis, a volume of interest is selected to be fully within the sample, avoiding the surface region. A typical volume of interest is 1028×772×98 voxels.

Structure Model Index (SMI) is measured using Scanco Medical's Bone Trabecular Morphometry evaluation with a threshold of 17. With this index the structural appearance of trabecular bone is quantified (see T. Hildebrand, P. Rüegsegger. Quantification of bone microarchitecture with the structure model index. *Comp Meth Biomech Biomed Eng* 1997; 1:15-23). The triangulated surface is dilated in normal direction by an infinitesimal amount, and the new bone surface and volume is calculated. By this, the derivative of the bone surface (dBS/dr) can be determined. The SMI is then represented by the equation:

$$SMI = 6 - \frac{BV \cdot \frac{dBS}{dr}}{BS^2}$$

SMI relates to the convexity of the structure to a model type. Ideal (flat) plates have an SMI of 0 (no surface change with dilation of the plates), whereas ideal cylindrical rods have an SMI of 3 (linear increase in surface with dilation of rods). Round spheres have an SMI of 4. Concave structure gives negative dBS/dr, resulting in negative SMI values. Artificial boundaries at the edge of the volume of interest are not included in the calculation and thus suppressed.

Gas Pycnometry Method

The Percent Open Cell Content is measured via gas pycnometry. Gas pycnometry is a common analytical technique that uses a gas displacement method to measure volume accurately. Inert gases, such as helium or nitrogen, are used as the displacement medium. The sample is sealed in the instrument compartment of known volume, the appropriate inert gas is admitted, and then expanded into another precision internal volume. The pressure before and after expansion is measured and used to compute the sample volume. Dividing this volume into the sample weight gives the gas displacement density.

The percentage of open cells can be determined by performing a test which uses Micromeritics' AccuPyc Pycnometer. The ASTM procedure D2856 describes 5 methods (A, B, C, D, and E) for determining the percent of open cells of foam materials.

For these experiments, the samples can be analyzed using an Accupyc 1340 using nitrogen gas with the ASTM foampyc software. Method C of the ASTM procedure is to be used to calculate to percent open cells. This method simply compares the geometric volume as determined using calipers and standard volume calculations to the true volume as measured by the Accupyc. It is recommended that these measurements be conducted by Micromeretics Analytical Services, Inc. (One Micromeritics Dr, Suite 200, Norcross, Ga. 30093). More information on this technique is available on the Micromeretics Analytical Services web sites (www.particletesting.com or www.micromeritics.com), or published in a book, "Analytical Methods in Fine particle Technology", by Clyde On and Paul Webb.

Star Volume Method

Cell interconnectivity can be determined via the Star Volume Method. Star Volume is a measure of the "openness" of the void space in a two phase structure. By choosing a random uniformly distributed set of points in the phase of interest (in our case this is the background), we can extend lines in random directions from each of these points. The lines are extended until they touch the foreground phase. The length of each of these lines is then recorded. The random points have a sampling of 10 in each direction (x/y/z) and at each point 10 random angles are chosen. If the line extends to the border of the ROI of interest that line is discarded (we only want to accept lines that actually intersect with the foreground phase). The final equation is based upon the research published in *Star volume in bone research. A histomorphometric analysis of trabecular bone structure using vertical sections*; Vesterby, A.; Anat Rec.; 1993 February; 235(2):325-334:

$$StarVolume = \frac{4}{3}\pi \cdot \frac{\sum dist^3}{N}$$

where "dist" is the individual distances and N is the number of lines examined.

Dry Density Method

The personal health care article and porous disintegratable solid substrate described herein can be characterized in terms of a dry density determination. Dry density is measured in grams/milliliter (g/ml).

The dry density of the health care article can be determined by dividing the weight of the health care article by the known volume of the health care article. The dry density of the porous disintegratable solid substrate can be determined by dividing the weight of the substrate by the known volume of the substrate. In order to determine the dry density, the weight measurements of the porous disintegratable solid substrate or personal health care article are made after the wet aerated mixture is dried and the porous disintegratable solid substrate has been at the desired moisture content for one hour.

After the wet aerated mixture is dried and the porous disintegratable solid substrate has been at the desired moisture content for one hour the volume can be determined by cutting the porous disintegratable solid substrate can be cut to known x-y dimensions and the thickness can be measured using the Thickness Method described above. Then the cut porous disintegratable solid substrate is weighed.

Wet Density Method

The wet aerated mixture described herein can be characterized in terms of a wet density determination. The wet density of the wet aerated mixture can be determined by dividing the weight of the wet aerated mixture by the known volume of the wet aerated mixture. In order to determine the wet density, the weight of the wet aerated mixture can be determined immediately after the wet aerated mixture is formed. The volume can be determined by removing an aliquot of known volume from the wet aerated mixture and then weighing the aliquot. The wet density is measured in grams/milliliter (g/ml)

EXAMPLES

The following examples further describe and demonstrate embodiments within the scope of the invention. The examples are given solely for the purpose of illustration and are not to be construed as limitations of the present invention, as many variations thereof are possible without departing from the spirit and scope of the invention.

Example 1

The following polymer mixture can be prepared for use during the preparation of the personal health care articles of the present invention:

| Component | Wt % |
|---|---|
| Polyvinyl alcohol (CEVOL 523)[1] | 20.06 |
| Distilled Water | q.s. to Volume |
| Total | 100 |

[1]CEVOL ® 523 available from Celanese Corporation (Dallas, Texas)

Example 1 can be made with the following procedure. The distilled water is put into an appropriately sized and cleaned vessel and then is stirred at 100-300 rounds per minute (rpm). The polyvinyl alcohol is weighed into a suitable container and is slowly added to the distilled water in small increments using a spatula while the distilled water is continuously stirred and forming visible lumps is avoided. The mixing speed is adjusted to minimize foam formation. The distilled water polyvinyl alcohol mixture is slowly heated to 85° C. while continuing to stir and then allowed to cool to room temperature. The distilled water polyvinyl alcohol mixture will appear hazy. The distilled water polyvinyl alcohol mixture is allowed to cool until it is at room temperature and is an amber colored clear solution. This room temperature, amber colored clear mixture is the polymer mixture.

Example 2

The following personal health care article can be prepared in accordance to the present invention:

| Component | Wt % |
|---|---|
| Polymer Mixture from Example 1 | 55.08 |
| Glycerin | 3.70 |
| Retail Cold & Flu Product[2] (Vicks ® NyQuil ® Cold& Flu (Cherry Flavor)) | 26.18 |
| Tween-60K[3] | 6.12 |
| Distilled Water | q.s. to Volume |
| Total | 100 |

[2]Vicks ® NyQuil ® Cold & Flu (Cherry Flavor) available from The Procter & Gamble Company (Cincinnati, Ohio).
[3]Tween-60K available from Croda Inc. (Edison, New Jersey)

Example 2 can be made with the following procedure. The polymer mixture from Example 1 is combined with the plasticizer, a health care active, a surfactant, and distilled water. All ingredients are mixed using a SpeedMixer™ DAC 400 FV (available from FlackTek, Inc., Landrum, S.C.). Then, approximately 223 g of the mixture is transferred to a Max 300 SpeedMixer™. Then, the mixture, which is at room temperature, is mixed at approximately 2,750 rpm for at least 30 seconds to form the mixture.

Approximately 218 g of the of the mixture is transferred into a 5 quart stainless steel bowl of a KitchenAid® Mixer Model K5SS (available from Hobart Corporation, Troy, Ohio) fitted with a flat beater attachment. The mixture is vigorously aerated at high speed for approximately 11 minutes to form a wet aerated mixture. An aliquot of the wet aerated mixture is removed from the stainless steel bowl and the density is measured. In Example 2, the wet density is approximately 0.29 g/cm$^3$. The remainder of the wet aerated mixture is spread evenly with a spatula into aluminum molds that are bottom-lined with Bytac® General Purpose film (available from Saint-Gobain, Paris, France). Each mold is placed into a 45° C. convection oven for 16 hours to dry. After drying, the porous disintegratable solid substrate is removed from the mold and cut into a square pad that weighs approximately 4 g to form the personal health care article.

Example 3

The following personal health care article can be prepared in accordance with the present invention:

| Component | Wt % |
|---|---|
| Polymer Mixture from Example 1 | 55.06 |
| Glycerin | 3.69 |
| Retail Cold & Flu product[4] (Vicks ® NyQuil ® Less Drowsy Cold & Flu (Cherry Flavor)) | 26.25 |
| Tween-60K | 6.06 |
| Distilled water | q.s. to Volume |
| Total | 100.00 |

[4]Vicks ® NyQuil ® Less Drowsy Cold & Flu (Cherry Flavor) is available from The Procter & Gamble Company (Cincinnati, Ohio)

Example 3 can be made according to the procedure in Example 2 except the mixture is vigorously aerated at high speed for approximately 6 minutes and the wet density is approximately 0.25 g/cm$^3$. After drying, the porous disintegratable solid substrate is removed from the mold and cut into a square pad that weighs approximately 4 g to form the personal health care article.

Example 4

The following personal health care article can be prepared in accordance to the present invention:

| Component | Wt % |
| --- | --- |
| Polymer Mixture from Example 1 | 55.14 |
| Glycerin | 3.73 |
| Retail digestive upset product[5] (Pepto Bismol ®) | 26.24 |
| Tween-60K | 5.97 |
| Distilled Water | q.s. to Volume |
| Total | 100.00 |

[5]Pepto Bismol ® is available from The Procter & Gamble Company (Cincinnati, Ohio)

Example 4 can be made according to the procedure in Example 2 except the mixture is vigorously aerated at high speed for approximately 4 minutes and the wet density is approximately 0.24 g/cm³. After drying, the porous disintegratable solid substrate is removed from the mold and cut into a square pad that weighs approximately 4 g to form the personal health care article.

Example 5

The following personal health care article can be prepared in accordance to the present invention:

| Component | Wt % |
| --- | --- |
| Polymer Mixture from Example 1 | 55.15 |
| Glycerin | 3.72 |
| Retail antacid product[6] (Mylanta ® Supreme (Cherry Flavor)) | 26.20 |
| Tween-60K | 6.00 |
| Distilled water | q.s. to Volume |
| Total | 100.00 |

[6]Mylanta ® Supreme (Cherry Flavor) available from Johnson & Johnson - Merck Consumer Pharmaceuticals (New Jersey)

Example 5 can be made according to the procedure in Example 2 except the mixture is vigorously aerated at high speed for approximately 10 minutes and the wet density is approximately 0.26 g/cm³. After drying, the porous disintegratable solid substrate is removed from the mold and cut into a square pad that weighs approximately 4 g to form the personal health care article.

Example 6

The following personal health care article can be prepared in accordance to the present invention:

| Component | Wt % |
| --- | --- |
| Polymer Mixture from Example 1 | 40.20 |
| Glycerin | 3.51 |
| Bismuth Subsalicylate[7] | 10.17 |
| Tween-60K | 5.46 |
| D&C Red #28 | 0.01 |
| Distilled Water | q.s. to Volume |
| Total | 100 |

[7]Bismuth Subsalicylate available from Alfa Aesar (Ward Hill, Massachusetts)

Example 6 can be made with the following procedure. The polymer mixture from Example 1 is combined with a plasticizer, a health care active, a surfactant, an aesthetic agent, and distilled water. All the ingredients are mixed using a SpeedMixer™ DAC 400 FV (available from FlackTek, Inc., Landrum, S.C.). Then, 200 g of the mixture is transferred to a Max 300 SpeedMixer™. Then, the mixture, which is at room temperature, is mixed at approximately 2,750 rounds per minute (rpm) for at least 30 seconds.

Approximately 194 g of the of the above mixture is transferred into a 5 quart stainless steel bowl of a KitchenAid® Mixer Model K5SS (available from Hobart Corporation, Troy, Ohio) fitted with a flat beater attachment. The mixture is vigorously aerated at high speed for approximately 16 minutes. An aliquot of the resulting wet aerated mixture is removed from the stainless steel bowl and the density is measured. In Example 6, the wet density is approximately 0.35 g/cm³. The wet aerated mixture is spread evenly with a spatula into aluminum molds that are bottom-lined with Bytac® General Purpose film (available from Saint-Gobain, Paris, France). Each mold is placed into a 45° C. convection oven for 16 hours to dry. After drying, the porous disintegratable solid substrate is removed from the mold and cut into a square pad that weighs approximately 1.4 g and contains approximately 524 mg of bismuth subsalicylate to form a personal health care article.

Example 7

The following personal health care article can be prepared in accordance to the present invention:

| Component | Wt % |
| --- | --- |
| Polymer Mixture from Example 1 | 40 |
| Glycerin | 3.5 |
| Acetaminophen[8] | 5 |
| Dextromethorphan | 0.15 |
| Doxylamine succinate | 0.063 |
| Tween-60K | 5 |
| FD&C red #40 | 0.01 |
| Sucralose | 0.05 |
| Cherry Flavor | 0.12 |
| Distilled Water | q.s. to Volume |
| Total | 100 |

[8]Acetaminophen is available from Sigma Aldrich (St. Louis, Missouri)

Example 7 can be made according to the procedure in Example 6 except the polymer mixture in Example 1 is combined with a plasticizer, health care actives, a surfactant, aesthetic agents, and distilled water and the mixture is vigorously aerated for about 10 minutes and the wet density is approximately 0.30 g/cm³. After drying, the porous disintegratable solid substrate is removed from the mold and cut into a square pad that weighs approximately 2.18 g and contains approximately 500 mg acetaminophen, 15 mg dextromethorphan, and 6.25 mg doxylamine succinate to form a personal health care article.

Example 8

The following personal health care article can be prepared in accordance to the present invention:

| Component | Wt % |
| --- | --- |
| Polymer Mixture from Example 1 | 40 |
| Glycerin | 3.5 |
| Calcium Carbonate[9] | 10 |

-continued

| Component | Wt % |
|---|---|
| Tween-60K | 5 |
| Distilled Water | q.s. to Volume |
| Total | 100 |

⁹Calcium carbonate available from Sigma Aldrich (St. Louis, Missouri)

Example 8 can be prepared according to the procedure in Example 7 except the polymer mixture in Example 1 is combined with a plasticizer, a health care active, a surfactant, and distilled water. After drying, the porous disintegratable solid substrate is removed from the mold and cut into square pads and each square pad that weighs approximately 1.32 g and contains approximately 500 mg calcium carbonate. A square pad is coated with a surface resident coating comprising naproxen sodium (Sigma Aldrich, product # N5160). The top surface of the square pad is brushed with a cotton swab dipped in distilled water. Immediately after brushing, 220 mg naproxen sodium is evenly distributed on the wetted surface of the square. The square pad with the naproxen surface resident coating is dried at room temperature for about 90 minutes to form the personal health care article.

Example 9

A personal health care article with multiple porous disintegratable solid substrates can be prepared in accordance to the present invention.

A. Substrate Containing Bismuth Subsalicylate

| Component | Wt % |
|---|---|
| Polymer Mixture from Example 1 | 40 |
| Glycerin | 3.5 |
| Bismuth Subsalicylate | 10 |
| Tween-60K | 5 |
| D&C Red #28 | 0.01 |
| Distilled Water | q.s. to Volume |
| Total | 100 |

B. Substrate Containing Calcium Carbonate

| Component | Wt % |
|---|---|
| Polymer Mixture from Example 1 | 40 |
| Glycerin | 3.5 |
| Calcium Carbonate | 10 |
| Tween-60K | 5 |
| Distilled Water | q.s. to Volume |
| Total | 100 |

Example 9 can be prepared according to the following procedure. Example 9A and 9B are prepared according to the procedure in Examples 7 except the polymer mixture in Example 1 is combined with a plasticizer, a health care active, a surfactant, an aesthetic agent, and distilled water in Example 9A and the polymer mixture in Example 1 is combined with a plasticizer, a health care active, a surfactant, and distilled water in Example 9B. After drying each porous disintegratable solid substrate is removed from the mold and cut into square pads with the same area. Each square pad in Example 9A weighs approximately 1.39 g and contains approximately 524 mg of bismuth subsalicylate. Each square pad in Example 9B weighs approximately 1.32 g and contains approximately 500 mg of calcium carbonate. In order to combine the porous disintegratable substrates to form a personal health care article the surface of the porous disintegratable solid substrate from Example 9A is lightly brushed with distilled water using a cotton swab. Immediately after, the porous disintegratable solid substrate from Example 9B is placed on top of the wet surface of the substrate from Example 9A. Gentle pressure is applied to each substrate for approximately 30 seconds to form the personal health care article. The resulting personal health care article will comprise two porous disintegratable solid substrates, one substrate containing bismuth subsalicylate and the substrate other calcium carbonate.

Example 10

Example 10 can be prepared according to the following procedure. The porous disintegratable solid substrate containing calcium carbonate from Example 9B is cut into a square pad weighing approximately 1.32 g and containing approximately 500 mg of calcium carbonate. Then, the square pad is injected with 20 mg of simethicone 4 times using a micropipetter for a total of 80 mg of simethicone to form the personal health care article. The resulting personal health care article contains an antacid, calcium carbonate, and an anti-flattulent, simethicone.

Example 11

The following personal health care article can be prepared in accordance to the present invention:

| Component | Wt % |
|---|---|
| Polymer Mixture from Example 1 | 55.04 |
| Glycerin | 3.78 |
| Phenylephrine | 1.0 |
| Tween-60K | 6.02 |
| Royal Blue Color | 0.01 |
| Distilled Water | q.s. to Volume |
| Total | 100 |

Example 11 can be made according to the procedure in Example 6 except the mixture is vigorously aerated for about 2 minutes and the wet density is approximately 0.22 g/cm³. After drying, the porous disintegratable solid substrate is removed from the mold and cut into tablets using an NP-RD10 Natoli Single Tablet Press (Thomas Engineering Inc., Hoffman Estates, Illinois) equipped with Extra Deep D tooling. Less than 0.1 tons of compression force is applied to the tablet press to cut the porous disintegratable solid substrate and form personal health care articles that are tablets.

Example 12

The following personal health care article can be prepared in accordance to the present invention:

| Component | Wt % |
|---|---|
| Polymer Mixture from Example 1 | 40 |
| Glycerin | 3.5 |
| Aspirin | 10 |

| Component | Wt % |
| --- | --- |
| Tween-60K | 5.5 |
| Distilled Water | q.s. to Volume |
| Total | 100 |

Example 12 can be made according to the procedure in Example 6 except the polymer mixture in Example 1 is combined with a plasticizer, a health care active, a surfactant, and distilled water. After drying, the porous disintegratable solid substrate is removed from the mold and cut into a square pad that weighs approximately 0.88 g and contains approximately 325 mg of aspirin to form a personal health care article. The personal health care article is then placed into 4 ounces of water and stirred until the personal health care article disintegrates. This mixture of the disintegrated personal health care article and the water provides a liquid dose of aspirin.

Example 13

A personal health care article with multiple porous disintegratable solid substrates can be prepared in accordance to the present invention.

| A. Substrate Containing Bismuth Subsalicylate | |
| --- | --- |
| Component | Wt % |
| Polymer Mixture from Example 1 | 40 |
| Glycerin | 3.5 |
| Bismuth Subsalicylate | 10 |
| Tween-60K | 5 |
| D&C Red #28 | 0.01 |
| Distilled Water | q.s. to Volume |
| Total | 100 |

| B. Substrate Containing Aesthetic Agents | |
| --- | --- |
| Component | Wt % |
| Polymer Mixture from Example 1 | 40 |
| Glycerin | 3.5 |
| FD&C blue #2 | 0.01 |
| Sucralose | 0.05 |
| Peppermint flavor | 0.1 |
| Tween-60K | 5 |
| Distilled Water | q.s. to Volume |
| Total | 100 |

Example 13 can be made according to the procedure in Example 9 except to make Example 13B the polymer mixture in Example 1 is combined with a plasticizer, a surfactant, aesthetic agents, and distilled water. After drying each porous disintegratable solid substrate is removed from the mold and cut into square pads with the same area. Each square pad in Example 13A weighs approximately 1.39 g and contains approximately 524 mg of bismuth subsalicylate. Each square pad in Example 13B weighs approximately 1 g. In order to combine the porous disintegratable substrates to form a personal health care article the surface of the porous disintegratable solid substrate from Example 13A is lightly brushed with distilled water using a cotton swab. Immediately after, the porous disintegratable solid substrate from Example 13B is placed on top of the wet surface of the substrate from Example 13A. Gentle pressure is applied to each square pad for approximately 30 seconds to form the personal health care article. The resulting personal health care article will comprise two porous disintegratable solid substrates, one substrate containing bismuth subsalicylate and the substrate other containing aesthetic agents.

Example 14

The following personal health care article can be prepared in accordance to the present invention:

| Component | Wt % |
| --- | --- |
| Polymer Mixture from Example 1 | 55 |
| Phenylephrine | 1 |
| Tween-60K | 6 |
| D&C Red #28 | 0.01 |
| Sucralose | 0.05 |
| Distilled Water | q.s. to Volume |
| Total | 100 |

Example 14 can be made according to the procedure in Example 6 except the polymer mixture in Example 1 is combined with a health care active, a surfactant, aesthetic agents, and distilled water. After drying, the porous disintegratable solid substrate is removed from the mold and cut into a square pad that weighs approximately 0.18 g and contains approximately 10 mg phenylephrine to form a personal health care article.

Example 15

The following personal health care article can be prepared in accordance to the present invention:

| Component | Wt % |
| --- | --- |
| Polymer Mixture from Example 1 | 40 |
| Glycerin | 3.5 |
| Calcium Carbonate | 10 |
| Sucralose | 0.05 |
| Wintergreen flavor | 0.1 |
| D&C Red #28 | 0.01 |
| Tween-60K | 5 |
| Distilled Water | q.s. to Volume |
| Total | 100 |

Example 15 can be made according to Example 6 except to make the polymer mixture in Example 1 is combined with a plasticizer, a health care active, aesthetic agents, a surfactant and distilled water. After drying, the porous disintegratable solid substrate is removed from the mold and cut into square pads. Each square pad weighs approximately 1.33 g and contains approximately 500 mg of calcium carbonate. A square pad is coated with a surface resident coating comprising naproxen sodium (Sigma Aldrich, product # N5160). The top surface of a square pad is brushed with a cotton swab dipped in distilled water. Immediately after brushing, 220 mg naproxen sodium is evenly distributed on the wetted surface of the pad. Then, the top surface of a second square pad is brushed with a cotton swab dipped in distilled water. Immediately after brushing, the wetted surface is placed on top of the surface of the first square pad that contains the naproxen surface resident coating such that the naproxen is located between the two square pads. Gentle pressure is applied to square pads for approximately 30 seconds and then allowed to dry for about 90 minutes at room temperature.

Example 16

The following personal health care article can be prepared in accordance to the present invention:

| Component | Wt % |
|---|---|
| Polyvinyl Alcohol | 8 |
| Glycerin | 3.5 |
| Calcium Carbonate | 10 |
| Tween-60K | 5 |
| Distilled Water | q.s. to Volume |
| Total | 100 |

Example 16 can be made with the following procedure. The distilled water is put into an appropriately sized and cleaned vessel and then is stirred at 100-300 rpm. The polyvinyl alcohol is weighed into a suitable container and is slowly added to the distilled water in small increments using a spatula while the distilled water is continuously stirred and forming visible lumps is avoided. The mixing speed is adjusted to minimize foam formation. The distilled water polyvinyl alcohol mixture is slowly heated to 85° C. while continuing to stir. Once the polyvinyl alcohol is dissolved add the plasticizer, the health care active, and the surfactant. Allow the mixture to cool to room temperature.

Approximately 194 g of the of the mixture is transferred into a 5 quart stainless steel bowl of a KitchenAid® Mixer Model K5SS (available from Hobart Corporation, Troy, Ohio) fitted with a flat beater attachment. The mixture is vigorously aerated at high speed for approximately 10 minutes. An aliquot of the resulting wet aerated mixture is removed from the stainless steel bowl and the density is measured. In Example 16, the wet density is approximately 0.30 g/cm$^3$. The wet aerated mixture is spread evenly with a spatula into aluminum molds that are bottom-lined with Bytac® General Purpose film (available from Saint-Gobain, Paris, France). Each mold is placed into a 45° C. convection oven for 16 hours to dry. After drying, the porous disintegratable solid substrate is removed from the mold. The porous disintegratable solid substrate is then cut into a square pad that weighs approximately 1.32 g and contains approximately 500 mg of calcium carbonate to form a personal health care article.

Example 17

The following personal health care article can be prepared in accordance to the present invention:

| Component | Wt % |
|---|---|
| Polymer Mixture from Example 1 | 64 |
| Glycerin | 3.0 |
| Phenylephrine | 1.0 |
| Tween-60K | 5.0 |
| Royal Blue Color | 0.01 |
| Distilled Water | q.s. to Volume |
| Total | 100.00 |

Example 17 can be made with the following procedure. The polymer mixture from Example 1 is combined with the plasticizer, a health care active, a surfactant, an aesthetic agent, and distilled water. All ingredients are mixed using a SpeedMixer™ DAC 400 FV (available from FlackTek, Inc., Landrum, S.C.). Then, approximately 200 grams of the mixture is transferred to a Max 300 SpeedMixer™. Then, the mixture, which is at room temperature, is mixed at approximately 2,750 rpm for at least 30 seconds to form the mixture.

Approximately 194 grams of the mixture is transferred into a 5 quart stainless steel bowl of a KitchenAid® Mixer Model K5SS (available from Hobart Corporation, Troy, Ohio) fitted with a flat beater attachment. The mixture is vigorously aerated at high speed for approximately 11 minutes to form a wet aerated mixture. An aliquot of the wet aerated mixture is removed from the stainless steel bowl and the wet density is measured. In Example 17, the wet density is approximately 0.20 g/ml. The remainder of the wet aerated mixture is spread evenly with a spatula into aluminum molds that are bottom-lined with Bytac® General Purpose film (available from Saint-Gobain, Paris, France). Each mold is placed into a 130° C. convection oven for approximately 40 min. After drying, a porous disintegratable solid substrate is removed from the mold and cut into a square pad that weighs approximately 0.218 grams and contains approximately 10 mg of phenylephrine to form the personal health care article.

Example 18

The following personal health care article can be prepared in accordance to the present invention:

| Component | Wt % |
|---|---|
| Polymer Mixture from Example 1 | 55.08 |
| Sorbitol[10] | 3.70 |
| Retail Cold & Flu Product[2] (Vicks ® NyQuil ® Cold& Flu (Cherry Flavor)) | 26.18 |
| Tween-60K[3] | 6.12 |
| Distilled Water | q.s. to Volume |
| Total | 100 |

[10]Sorbitol available from Roquette America (Keokuk, Iowa)

Example 18 can be made according to the procedure in Example 2.

Example 19

The following personal health care article can be prepared in accordance to the present invention:

| Component | Wt % |
|---|---|
| Polymer Mixture from Example 1 | 55.06 |
| Polyethylene Glycol[11] | 3.69 |
| Retail Cold & Flu product (Vicks ® NyQuil ® Less Drowsy Cold & Flu (Cherry Flavor)) | 26.25 |
| Tween-60K | 6.06 |
| Distilled water | q.s. to Volume |
| Total | 100.00 |

[11]Polyethylene Glycol available from Dow Chemical (Plaquemine, Louisiana)

Example 19 can be made according to the procedure in Example 3.

Example 20

The following personal health care article can be prepared in accordance to the present invention:

| Component | Wt % |
| --- | --- |
| Polymer Mixture from Example 1 | 55.14 |
| Glycerin | 3.73 |
| Retail digestive upset product (Pepto Bismol ®) | 26.24 |
| Tween-80[12] | 5.97 |
| Distilled Water | q.s. to Volume |
| Total | 100.00 |

[12]Tween-80 is available from Croda Inc. (Edison, New Jersey)

Example 20 can be made according to the procedure in Example 4.

Example 21

The following personal health care article can be prepared in accordance with the present invention:

| Component | Wt % |
| --- | --- |
| Polymer Mixture from Example 1 | 40 |
| Glycerin | 3.5 |
| Acetaminophen[8] | 5 |
| Dextromethorphan | 0.15 |
| Doxylamine succinate | 0.063 |
| PEG 40 Stearate[13] | 5 |
| FD&C red #40 | 0.01 |
| Sucralose | 0.05 |
| Cherry Flavor | 0.12 |
| Distilled Water | q.s. to Volume |
| Total | 100 |

[13]PEG 40 Stearate is available from Croda Inc. (Edison, New Jersey)

Example 21 can be made according to the procedure in Example 7.

Example 22

The following polymer mixture can be prepared for use during the preparation of the personal health care articles of the present invention:

| Component | Wt % |
| --- | --- |
| Polyvinyl Povidone[14] | 20.06 |
| Distilled Water | q.s. to Volume |
| Total | 100 |

[13]Polyvinylpovidone is available from BASF (Florham Park, NJ)

Example 22 can be made with the following procedure. The distilled water is put into an appropriately sized and cleaned vessel and then is stirred at 100-300 rounds per minute (rpm). The polyvinyl povidone is weighed into a suitable container and is slowly added to the distilled water in small increments using a spatula while the distilled water is continuously stirred and forming visible lumps is avoided. The mixing speed is adjusted to minimize foam formation. The distilled water polyvinyl povidone mixture is slowly heated to 85° C. while continuing to stir and then allowed to cool to room temperature. The distilled water polyvinyl povidone mixture is allowed to cool until it is at room temperature and is the polymer mixture.

Example 23

The following personal health care article can be prepared in accordance with the present invention:

| Component | Wt % |
| --- | --- |
| Polymer Mixture from Example 22 | 55.08 |
| Glycerin | 3.70 |
| Retail Cold & Flu Product (Vicks ® NyQuil ® Cold& Flu (Cherry Flavor)) | 26.18 |
| Tween-60K | 6.12 |
| Distilled Water | q.s. to Volume |
| Total | 100 |

Example 23 can be made according to the procedure in Example 2.

Example 24

The following polymer mixture can be prepared for use during the preparation of the personal health care articles of the present invention:

| Component | Wt % |
| --- | --- |
| Polyvinyl Alcohol | 19.06 |
| Methylcellulose[15] | 2.00 |
| Distilled Water | q.s. to Volume |
| Total | 100 |

[15] Methylcellulose (METHOCEL ®) available from Dow Chemical Co (Midland, Michigan)

Example 24 can be made with the following procedure. The distilled water is put into an appropriately sized and cleaned vessel and then is stirred at 100-300 rounds per minute (rpm). The polyvinyl alcohol is weighed into a suitable container and is slowly added to the distilled water in small increments using a spatula while the distilled water is continuously stirred and forming visible lumps is avoided. The mixing speed is adjusted to minimize foam formation. The mixture is slowly heated to 85° C. The methylcellulose is weighed into a suitable container and is slowly added to the heated mixture of polyvinyl alcohol and distilled water. The distilled water, polyvinyl alcohol, and methylcellulose mixture is allowed to cool until it is at room temperature and is the polymer mixture.

Example 25

The following personal health care article can be prepared in accordance with the present invention:

| Component | Wt % |
| --- | --- |
| Polymer Mixture from Example 24 | 55.06 |
| Glycerin | 3.69 |
| Retail Cold & Flu product (Vicks ® NyQuil ® Less Drowsy Cold & Flu (Cherry Flavor)) | 26.25 |
| Tween-60K | 6.06 |
| Distilled water | q.s. to Volume |
| Total | 100.00 |

Example 25 can be made according to the procedure in Example 3.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A personal health care article comprising at least one porous disintegratable solid substrate comprising:
   a. from about 1% to about 70%, by weight of the substrate, of a surfactant;
   b. from about 10% to about 70%, by weight of the substrate, of a polymer wherein the polymer has a weighted average molecular weight of from about 40,000 Da to about 500,000 Da;
   c. from about 0.025% to about 85%, by weight of the substrate, of a respiratory agent selected from the group consisting of nasal decongestants, mucolytics, expectorants, antihistamines, non-narcotic antitussives, demulcents, anesthetics, and combinations thereof; and
   d. an aesthetic agent selected from the group consisting of flavors, sensates, sweeteners, salivation agents, and combinations thereof;
   wherein the porous disintegratable solid substrate comprises a percent open cell content from about 85% to about 100% and wherein the article is orally ingestible and swallowable.

2. The article of claim 1, wherein the surfactant is selected from the group consisting of anionic surfactants, phospholipid surfactants, nonionic surfactants, and combinations thereof.

3. The article of claim 1, wherein the surfactant is a nonionic surfactant selected from the group consisting of myristyl alcohol, alpha tocopherol, glyceryl monooleate, macrogol 15 hydroxystearate, polyoxyethylene sorbitan fatty acid esters, polyoxylglycerides, sorbitan esters, and combinations thereof.

4. The article of claim 1, wherein the polymer is selected from the group consisting of naturally sourced polymers, cellulose derivatives, fiber polymers, carbomers, polymethacrylates, other synthetic polymers, and combinations thereof.

5. The article of claim 1, wherein the respiratory agent is selected from the group consisting of delayed release health care actives, extended release health care actives, immediate release health care actives, and combinations thereof.

6. The article of claim 1, wherein the article further comprises less than about 30%, by weight of the substrate, a plasticizer.

7. The article of claim 1, wherein the porous disintegratable solid substrate has a dry density of from about 0.03 g/cm$^3$ to about 0.50 g/cm$^3$.

8. The article of claim 1, wherein the porous disintegratable solid substrate has a wall thickness of from about 0.02 mm to about 0.15 mm.

9. The article of claim 1, further comprising a surface resident coating.

10. The article of claim 9, wherein the surface resident coating comprises one or more health care actives.

11. The article of claim 9, wherein the surface resident coating comprises one or more aesthetic agents.

12. The article of claim 9, wherein the surface resident coating is a powder.

13. The article of claim 9, wherein the surface resident coating covers an outer surface of the porous disintegratable solid substrate.

14. The article of claim 1, wherein the article comprises a first porous disintegratable solid substrate and a second porous disintegratable solid substrate, and wherein the health care active is situated between the first porous disintegratable solid substrate and the second porous disintegratable solid substrate.

15. A method of delivering a health care active comprising the steps of:
   a. nistering to a mammal the personal care article of claim 1; and
   b. ingesting said article.

16. A personal health care article comprising at least one porous disintegratable solid substrate comprising:
   a. from about 1% to about 70%, by weight of the substrate, of a surfactant;
   b. from about 10% to about 70%, by weight of the substrate, of a polymer wherein the polymer has a weighted average molecular weight of from about 40,000 Da to about 500,000 Da;
   c. from about 0.025% to about 85%, by weight of the substrate, of a gastrointestinal agent selected from the group consisting of anti-diarrheals, lower gastrointestinal agents, laxatives, anti-emetics, antacids, anti-flatulents, $H_2$ receptor antagonists, proton pump inhibitors, lipase inhibitors, rafting agents, and combinations thereof; and
   d. an aesthetic agent selected from the group consisting of flavors, sensates, sweeteners, salivation agents, and combinations thereof;
   wherein the porous disintegratable solid substrate comprises a percent open cell content from about 85% to about 100% and wherein the article is orally ingestible and swallowable.

17. The article of claim 16, wherein the surfactant is selected from the group consisting of myristyl alcohol, alpha tocopherol, glyceryl monooleate, macrogol 15 hydroxystearate, polyoxyethylene sorbitan fatty acid esters, polyoxylglycerides, sorbitan esters, and combinations thereof.

18. The article of claim 16, wherein the polymer is selected from the group consisting of naturally sourced polymers, cellulose derivatives, fiber polymers, carbomers, polymethacrylates, other synthetic polymers, and combinations thereof.

19. The article of claim 16, wherein the porous disintegratable solid substrate has a wall thickness of from about 0.02 mm to about 0.15 mm.

20. The article of claim 16, wherein the porous disintegratable solid substrate has a dry density of from about 0.03 g/cm$^3$ to about 0.50 g/cm$^3$.

21. A personal health care article comprising at least one porous disintegratable solid substrate comprising:
   a. from about 1% to about 70%, by weight of the substrate, of a surfactant;
   b. from about 10% to about 70%, by weight of the substrate, of a polymer;
   c. from about 0.025% to about 85%, by weight of the substrate, of a respiratory agent selected from the group consisting of nasal decongestants, mucolytics, expectorants, antihistamines, non-narcotic antitussives, demulcents, anesthetics, and combinations thereof; and
d. an aesthetic agent selected from the group consisting of flavors, sensates, sweeteners, salivation agents, and combinations thereof;

wherein the porous disintegratable solid substrate comprises a percent open cell content from about 85% to about 100%; wherein the article is orally ingestible and swallowable; and wherein the porous disintegratable solid substrate has a wall thickness of from about 0.02 mm to about 0.15 mm.

22. A personal health care article comprising at least one porous disintegratable solid substrate comprising:
   a. from about 1% to about 70%, by weight of the substrate, of a surfactant;
   b. from about 10% to about 70%, by weight of the substrate, of a polymer;
   c. from about 0.025% to about 85%, by weight of the substrate, of a gastrointestinal agent selected from the group consisting of anti-diarrheals, lower gastrointestinal agents, laxatives, anti-emetics, antacids, anti-flatulents, $H_2$ receptor antagonists, proton pump inhibitors, lipase inhibitors, rafting agents, and combinations thereof; and
   d. an aesthetic agent selected from the group consisting of flavors, sensates, sweeteners, salivation agents, and combinations thereof;

wherein the porous disintegratable solid substrate comprises a percent open cell content from about 85% to about 100%;

wherein the article is orally ingestible and swallowable; and wherein the porous disintegratable solid substrate has a wall thickness of from about 0.02 mm to about 0.15 mm.

* * * * *